United States Patent [19]

Weber et al.

[11] Patent Number: 5,227,298

[45] Date of Patent: Jul. 13, 1993

[54] METHOD FOR MICROENCAPUSLATION OF CELLS OR TISSUE

[75] Inventors: Collin J. Weber, Leonia, N.J.; Janet E. Norton, Scranton, Pa.; Keith Reemtsma, New York, N.Y.

[73] Assignee: The Trustees of Columbia University in the City of New York, New York, N.Y.

[21] Appl. No.: 568,821

[22] Filed: Aug. 17, 1990

[51] Int. Cl.$^5$ .................. C12N 11/10; C12N 11/04
[52] U.S. Cl. ............................ 435/178; 424/424; 424/493; 424/497; 264/4.3; 264/4.32; 264/4.33
[58] Field of Search ............. 264/4.32, 4.3, 4.33; 427/213.31; 435/182, 178; 428/402.2; 424/424, 493, 497

[56] References Cited

U.S. PATENT DOCUMENTS

| | | | |
|---|---|---|---|
| 4,352,883 | 10/1982 | Lim | 435/182 X |
| 4,391,909 | 7/1983 | Lim | 435/178 |
| 4,663,286 | 5/1987 | Tsang et al. | 435/182 X |
| 4,673,566 | 6/1987 | Goosen et al. | 435/178 X |
| 5,084,350 | 1/1992 | Chang et al. | 264/4.1 X |

FOREIGN PATENT DOCUMENTS 8904657  6/1989  PCT Int'l Appl. ............. 435/178

OTHER PUBLICATIONS

Colton, C. K. et al., *Journal of Biomechanical Engineering*, vol. 113, pp. 152–170 (May 1991).

Weber, C. et al., *Transplantation Proceedings*, vol. 23, No. 1, pp. 764–766 (Feb. 1991).

*Primary Examiner*—Robert L. Stoll
*Assistant Examiner*—John M. Covert
*Attorney, Agent, or Firm*—John P. White

[57] ABSTRACT

The subject invention provides a method of encapsulating viable tissue or cells within a double walled bead, the double-walled bean produced as a result of the method, as well as a method of pretreating the tissue or cells with an immunosuppressant such as UV-B irradiation prior to their encapsulation.

12 Claims, 29 Drawing Sheets

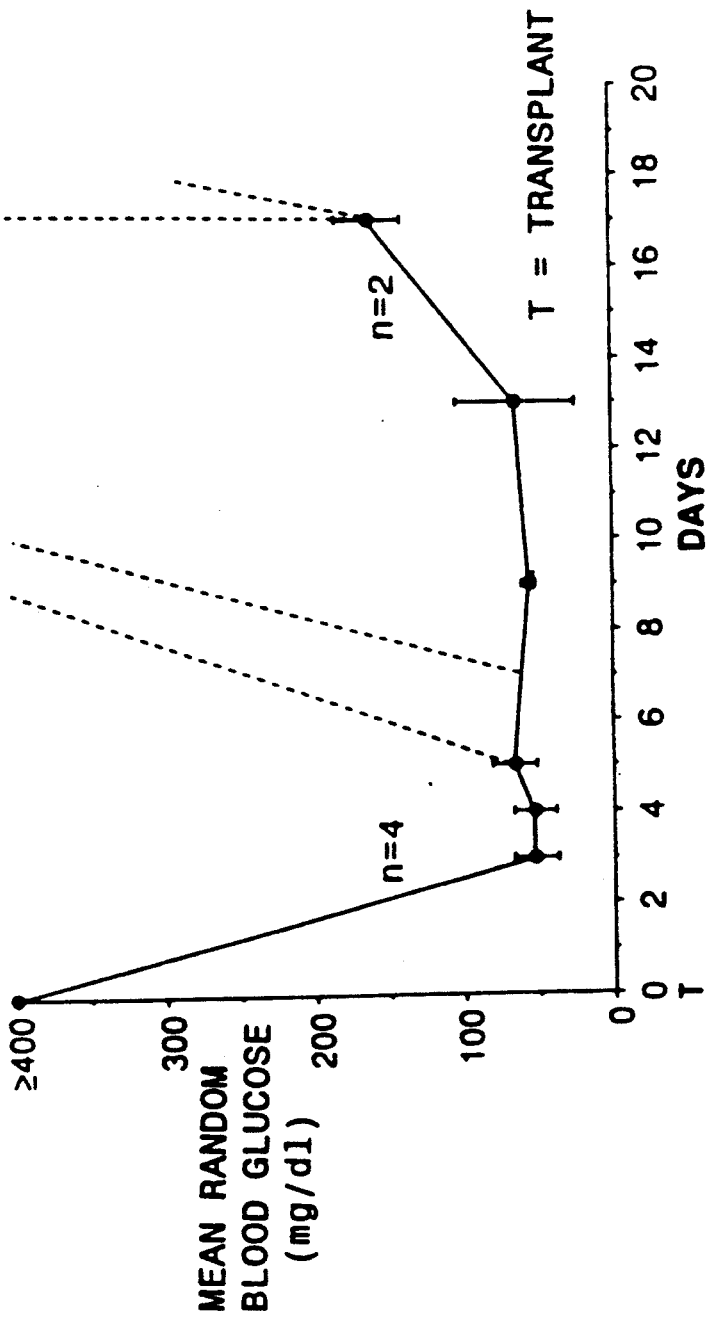

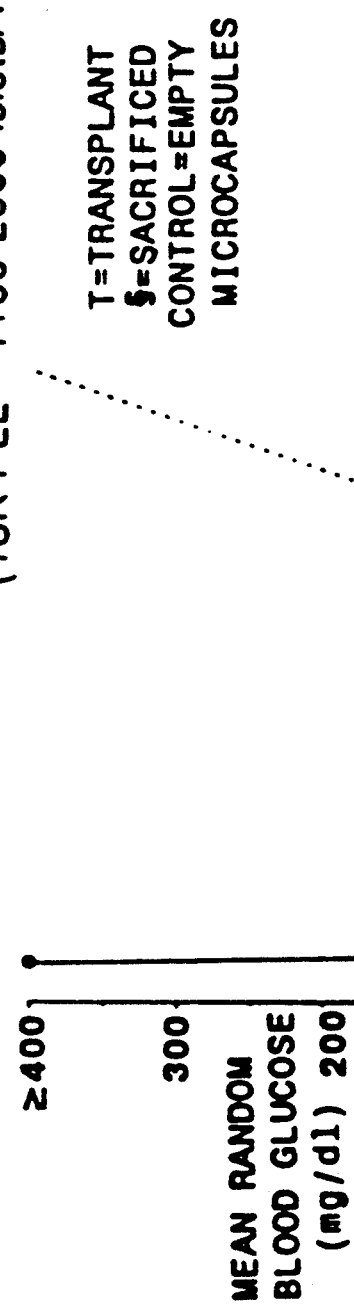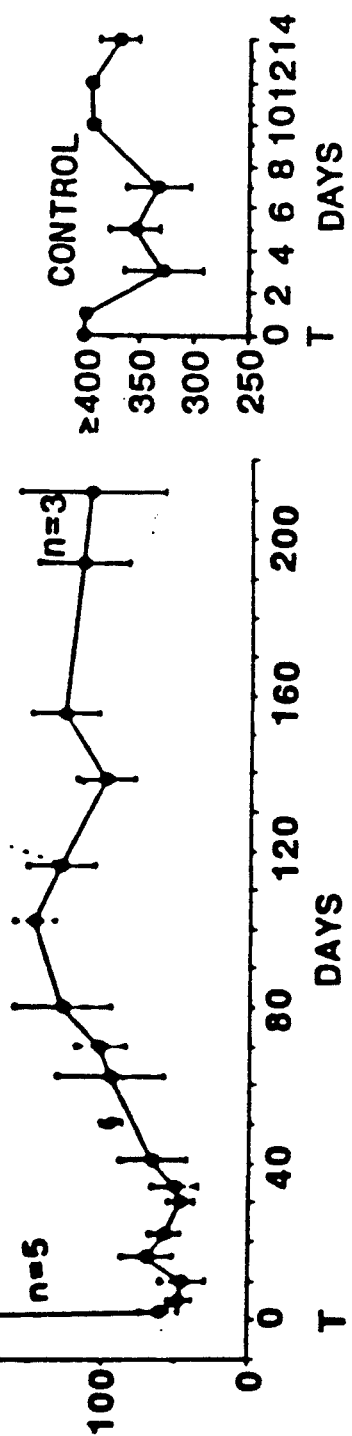
FIGURE 9A
IP Xenografts: Encapsulated Rat Islets into Unmodified C-57 Mouse Recipients
(18K PLL ~1100-2000 Islets/Tx)
FIGURE 9B

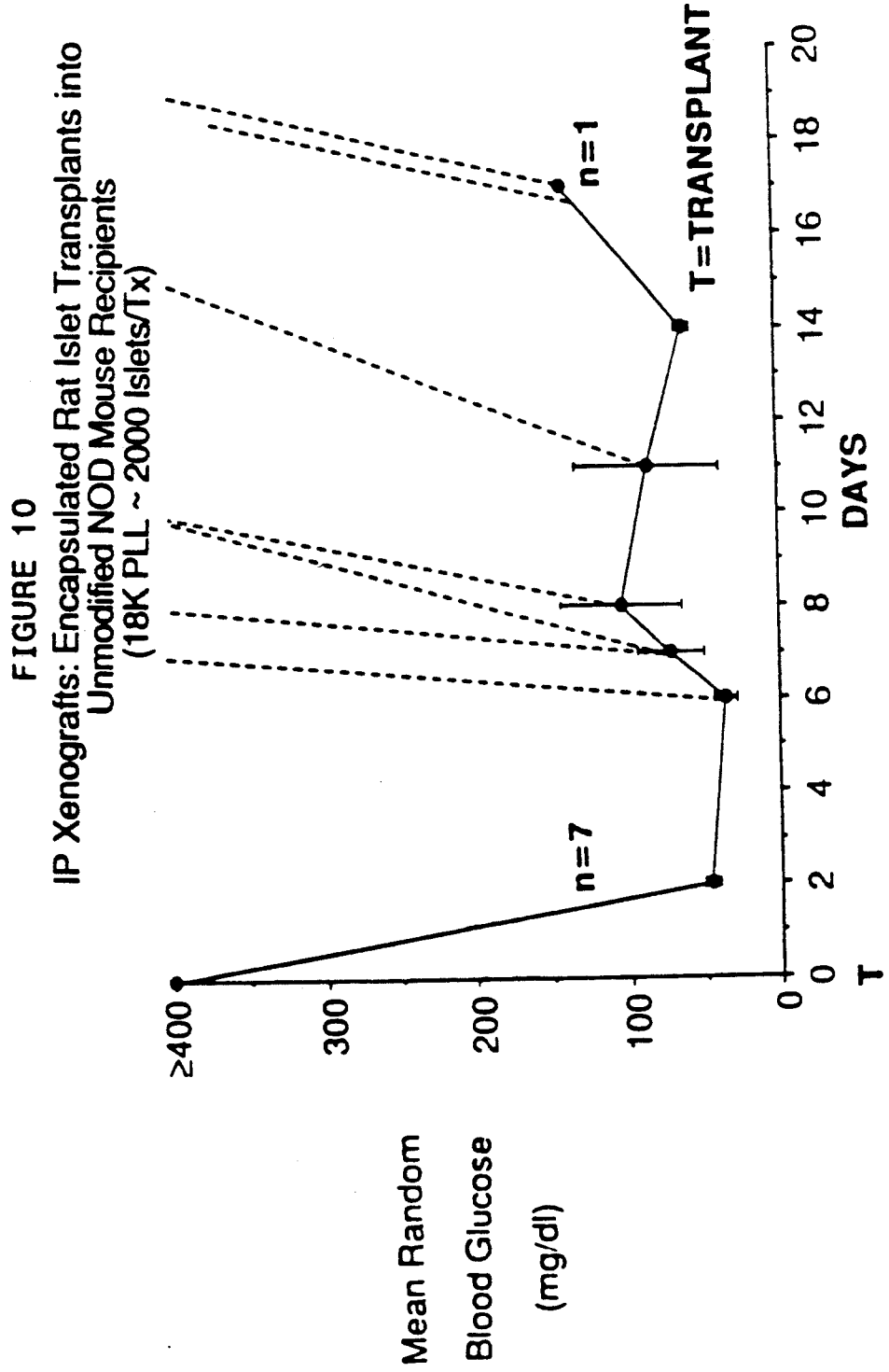

IP Xenografts: Encapsulated Rat Islets into Modified NOD Mouse Recipients (18K PLL - 2000 Islets/Tx)

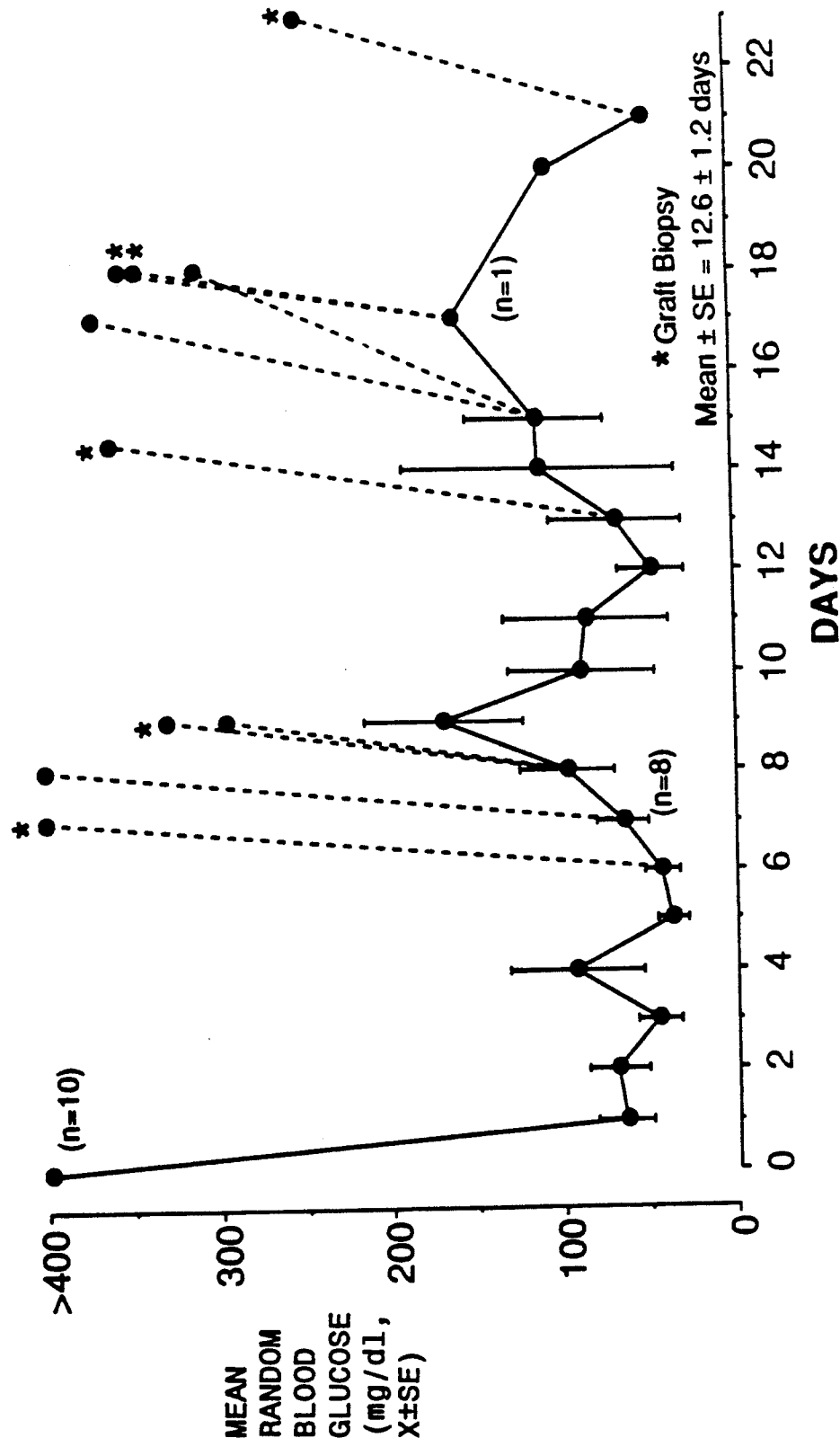

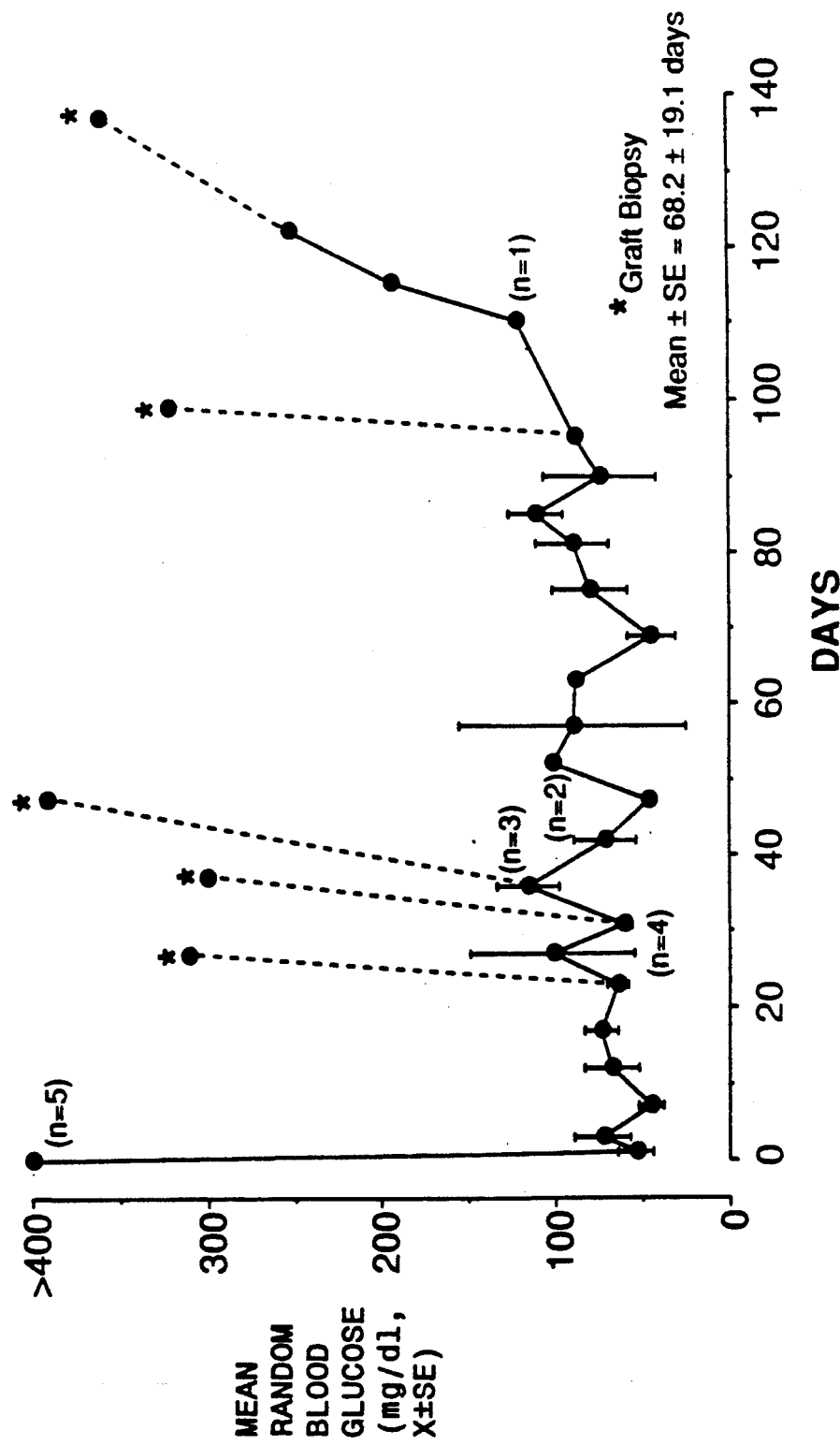

METHOD FOR MICROENCAPUSLATION OF CELLS OR TISSUE

BACKGROUND OF THE INVENTION

Pancreatic islet transplantation remains an attractive potential form of therapy for patients with diabetes mellitus. However, allografts of donor human islets have not been successful (Hering, B. et al. Horm Metab Res 1988 20:537). Availability and yield of viable, isolated human islets is likely to remain extremely limited. Ultimately, islet graft therapy for large numbers of patients will require the use of donor islets harvested from animals (xenografts). The only animals that are relatively closely related to man (that is, concordant xenografts) are the subhuman primates. Unfortunately, availability of these potential donors of islets is extremely limited. Therefore, it is logical to investigate the potential utility of a variety of widely unrelated animal sources of islets (discordant xenografts). Microencapsulation of donor islets is the most promising approach to long-term survival of islet xenografts.

METABOLIC FUNCTION OF DISCORDANT ISLET XENOGRAFTS

An obvious precondition of animal-to-human islet xenografts is some assurance that normal glucose homeostasis can be achieved. There are relatively few studies in the literature which have examined the metabolic function of totally unrelated (discordant) islet xenografts; however, in general, normalization of blood glucose has been observed during the interval prior to islet xenograft rejection. (Weber, C., et al., Transplant Proc 1986 18:823; Chabot, J., et al., Transplant Proc 1987 19:1160; Weber, C., et al., 1975 Surgery 77:208; Reemtsma, K., et al., In Friedman, E. and F. L'Esperance, Jr. eds. Diabetic Renal-Retinal Syndrome III, New York: Grune and Stratton, 1986:521; Reemtsma, K., et al., In Andrade, J., ed. Artificial Organs. Deerfield, Fla: VCH Publ., 1987:393; Warnock, G., et al. Diabetes 1989 38(Supp.1):1136); Wilson, D., et al., Diabetes 1989 38(Suppl.1):217; Ricordi, C., et al., Diabetes 1986 35:649; Lacy, P., et al. Diabetes 1982; 31(Suppl.4):109; Lake S., et al. Diabetes 1989 38:244). Virtually without exception, published studies have relied upon rodents with induced diabetes as recipients of islet xenografts. The metabolic function of animal islets in human diabetic recipients is entirely speculative. Optimistic predictions of normoglycemia following xenografting of porcine, rabbit, canine and bovine islets into humans are based upon similarities of amino acid sequences of insulin and nutrient-stimulated insulin secretory responses (Reemtsma, K., et al., In: Friedman, E. and F. L'Esperance, Jr. eds. Diabetic Renal-Retinal Syndrome III. New York: Grune and Stratton 1986:521; Reemtsma, K., et al., 1987 In Andrade, J. Ed., Artificial Organs. Deerfield, Fla: VCH Publ. 1987:393; Ricordi, C., et al., Diabetes 1986 35:649; Lacy, P., et al., Diabetes 1982 31(Suppl.4):109; Lake S., et al., Diabetes 1989 38:244; and Phillips, R. and L. Panepinto In: Tumbleson M., ed. Swine in Biomedical Research. New York: Plenum 1986:549. Aside from concerns about glucose insensitivity of ruminants, parameters of islet function are remarkably similar in higher mammals.

IMMUNOLOGIC DESTRUCTION OF ISLET XENOGRAFTS

Currently, there are no clinically relevant, safe immunological methods available which will achieve long-term survival by preventing the destruction of a discordant islet xenograft (Auchincloss, J., Jr. Transplantation 1988 46:1; Lafferty, K., 1988 In: R. Van Schilfgaarde and M. Hardy, eds. Transplantation of the Endocrine Pancreas in Diabetes Mellitus. Elsevier, Amsterdam; Reemtsma, K. and Weber, C. In: D. Sabiston, Jr., ed. The Sabiston Textbook of Surgery, 13th edn. Pa, USA: WB Saunders 1986:469). As summarized recently by Auchincloss (Auchincloss, J., Jr., supra), the conclusion of a large number of xenograft experiments is that ". . . the xenogeneic response is mediated, at large in part, by the same cellular mechanisms responsible for allograft rejection"; but that " . . . prolongation of xenografts, even in models of cell-mediated rejection, has generally been more difficult to achieve the greater the evolutionary divergence of the species combinations"; and that " . . . it is unknown whether the greater difficulty in prolonging xenografts is the result of quantitatively stronger cell-mediated rejection or of qualitatively different, perhaps unrecognized, mechanisms of xenograft rejection."

Several recent studies have suggested that the destruction of discordant islet xenografts is mediated by lymphocytes. Applicants found that anti-lymphocyte serum treatment of recipient diabetic mice plus donor or subhuman primate islet treatment in vitro with ultraviolet-B irradiation allowed prolonged (although not indefinite) islet xenograft survival (Weber, C., et al., Transplant Proc 1986 18:823 and Chabot, J., et al., Transplant Proc 1987 19:1160). Ricordi, et al. (Ricordi, C., et al., Proc Natl Acad Sci USA 1987 84:8080) found that low-temperature culture of donor human islets plus in vivo treatment with anti-CD4 (helper T-cell) monoclonal antibody (MoAb) produced marked prolongation (but not indefinite survival) of human-to-mouse islet xenografts. Wilson, et al. (Wilson, D., et al., Diabetes 1989 38(Suppl.1:217) found that depletion of helper T-lymphocytes by treatment of recipient mice with anti-CD4 MoAb allowed histological survival of fetal pig proislets for up to four weeks. Treatment of recipient mice with MoAb against cytotoxic (CD8+) T-cells had no beneficial effect (Wilson, et al., supra). Pierson, et al. (Pierson R., et al. Transplant Proc (in press) found that anti-CD4 MoAb treatment prolonged monkey-to-mouse skin xenograft survival, while anti-CD8 or cyclosporine treatment had little effect when used singly. When used with anti-CD4, both cyclosporine and anti-CD8 MoAb treatments produced significant monkey-to-mouse skin xenograft survival (Pierson R., et al. Transplant Proc (in press).

These data are consistent with the results of Kaufman, et al. (Kaufman, D., et al., Transplantation 1988 46:210), who found that depletion of recipient helper T cells with anti-CD4 MoAb resulted in prolonged (but not indefinite) survival of more closely related (concordant) rat-to-mouse islet xenografts; and that a combination of anti-CD4 therapy with anti-Ia immunodepletion of donor rat islets resulted in indefinite (concordant) islet xenograft survival (Kaufman, D., et al., supra).

The observation of Kaufman et al. (Kaufman, D., et al., Transplantation 1988 46:210) are consistent with the hypothesis put forward by Auchincloss (Auchincloss, J., Jr. Transplantation 1988 46:1), namely, that discordant xenografts are more difficult to prolong than are concordant xenografts. These findings also are in keeping with reports that more closely related islet allografts may be prolonged indefinitely by several immunological maneuvers, such as recipient treatment with antibody to helper T-cells or treatment of donor islet preparation with antibodies to Ia+ dendritic cells (Shizuru, J., et al., 1987 Science 237:278; Faustman, D., et al., Proc Natl Acad Sci USA 1981 78:5156; Lacy, P. In: Alberti K. and L. Krall, eds. The Diabetes Annual/3. Amsterdam: Elsevier 1987:189). Unfortunately, these relatively nontoxic methods are ineffective with discordant xenografts, while more effective host manipulations, such as lethal whole-body irradiation, total lymphoid irradiation, ablative chemotherapy and induction of hematopoietic chimerism (Qin, S., et al., J Exp Med 1989 1169:779; Mayumi, H. and Good, R. J Exp Med 1989 169:2113) are probably too invasive vis-a-vis the severity of the disease they might be employed to cure, namely, diabetes mellitus.

PROTECTION OF ISLET XENOGRAFTS WITH MECHANICAL BARRIERS

Since indefinite survival of a totally unrelated islet xenograft has not been achieved using immunologic manipulations, several investigators have examined the usefulness of porous membranes and envelopes as mechanical protective barriers against host immunocytes. The rationale for success with such interposed membranes is that cell-cell contact is required for cell-mediated cytotoxicity. In general, short-term islet xenograft function has been noted, with graft failure occurring as a result of an inflammatory response to the membrane material (Scharp, D., et al., World J Surg 1984 8:221; Altman, J., et al.; Diabetes 1986 35:625).

Recently, a new approach to mechanical protection of islets has been introduced. This technique, called "microencapsulation," involves creation of multiple, porous poly-amino acid-alginate microspheres which contain donor islets (Weber, C., et al., Surgery 1975 77:208; Reemtsma, K. and C. Weber. In: D. Sabiston, Jr. ed. The Sabiston Textbook of Surgery, 13th edn. WB Saunders, Phila. 1986:469; O'Shea, G. and A. Sun. Diabetes 1986 35:943; Darquy, S. and G. Reach. Diabetologia 1985 28:776; Ricker, A., et al. In: M. Jaworski ed. The Immunology of Diabetes Mellitus. Amsterdam: Elsevier 1986:193; Norton, J., et al. In: R. Van Schifgaarde and M. Hardy, eds. Transplantation of the Endocrine Pancreas in Diabetes Mellitus. Amsterdam: Elsevier 1988:308). This method is extremely promising for the future of islet xenografting, because the microcapsule surface is remarkably biocompatible, as evidenced by the fact that empty microcapsules excite little or no cellular reaction when placed in the peritoneal cavity of rodents. (Ricker, A., et al. supra; Norton, J. et al., supra; Calafiore, R. et al., Diabetes 1989 38(Suppl.1):297; Calafiore, R. et al. Clinical Res 1987 35:499A; Ricker, A. et al., Cold Spring Harbor Symposium in Immunology of Diabetes, Abstracts, 1987).

O'Shea and Sun found that concordant islet xenografts into streptozotocin-diabetics functioned for a mean of 80 days (O'Shea G. and Sun. A., Diabetes 1986 35:943). "Varying degrees of cell overgrowth" were noted around microcapsules biopsied at sacrifice of recipient mice, and "no viable islets were found (within microcapsules)" (O'Shea G. and Sun A.). Ricker, et al. (Ricker, A., et al., In: Jaworski M., ed. The Immunology of Diabetes Mellitus. Amsterdam: Elsevier, 1986:1193) found that microencapsulated rat islets functioned for more than 80 days in streptozotocin-diabetic mice, with minimal or no cellular reaction and some identifiable islets within microcapsules at graft biopsy. These results were confirmed in applicants' laboratory (Norton J., et al., In: Van Schilfgaarde R. and Hardy M., eds. Transplantation of the Endocrine Pancreas in Diabetes Mellitus. Amsterdam: Elsevier, 1988:308; and Weber C., et al., Xenograft/25. Amsterdam: Elsevier, 1989).

The novelty of the present invention over the prior art is in the creation of a double wall of poly-lysine-alginate layering, which is functionally superior to prior single-wall designs of microcapsules because fewer deformed microcapsules are found in the solution following preparation of microcapsules (deformed capsules are more vulnerable to breakage than normal capsules). In addition, donor islets obtained from dog and cat species will function for prolonged periods of time, compared to prior data, when these donor islets are protected within double-walled, as opposed to single-walled microcapsules, and then xenotransplanted into the peritoneal cavities of recipient, diabetic mice.

Another aspect of the present invention which is novel over the prior art is the use of UV-B treated islets which are encapsulated and transplanted into a subject. These UV-B treated encapsulated islets function longer than non-UV-B treated, encapsulated islets. The applicants have concluded that the techniques of UV-B and microencapsulation are synergistic in the prevention of destruction of islet xenografts.

SUMMARY OF THE INVENTION

The subject invention provides a method of encapsulating viable tissue or cells within a double-walled bead comprising:
  (a) suspending the tissue or cells in an aqueous medium which is physiologically compatible with the tissue and which contains a water soluble substance which
      (i) is physiologically compatible with the tissue; and
      (ii) can be gelled to form a bead;
  (b) forming the suspension into droplets of a size sufficient to encapsulate the tissue or cells;
  (c) treating the droplets so as to form discrete, shape-retaining temporary capsules;
  (d) forming a permanent semipermeable membrane around the temporary capsules so as to obtain a single-walled bead encapsulating the tissue or cells; and
  (e) contacting the resulting single-walled bead with the water soluble substance under conditions such that a second membrane is formed so as to thereby obtain a double-walled bead encapsulating the tissue or cells.

BRIEF DESCRIPTION OF THE FIGURES

FIG. 8 Random blood glucose value ($\bar{x} \pm SEM$) following encapsulated canine islet xenografts (i.p.) into spontaneously diabetic NOD mice. Dotted lines represent rejections of individual animals.

FIG. 9 Random blood glucose ($\bar{x} \pm SEM$) following i.p. xenografts of encapsulated rat islets into unmodified SZN-diabetic C57BL/6J mice. Dotted line indicates graft failure of one animal. Insert: blood glucose of control mice receiving empty microcapsules (n=6).

FIG. 10 Random blood glucose ($\bar{x} \pm SEM$) of unmodified NOD mice following intraperitoneal xeno-transplantation of microencapsulated rat islets. Dotted lines represent graft failure of individual mice.

FIG. 28 IP xenografts: Encapsulated rat islet transplants into unmodified NOD mouse recipients.

FIG. 29 UV-B treated, microencapsulated intraperitoneal rat-to-NOD mouse islet xenografts (no immunosuppression).

DETAILED DESCRIPTION OF THE INVENTION

Figure 1:
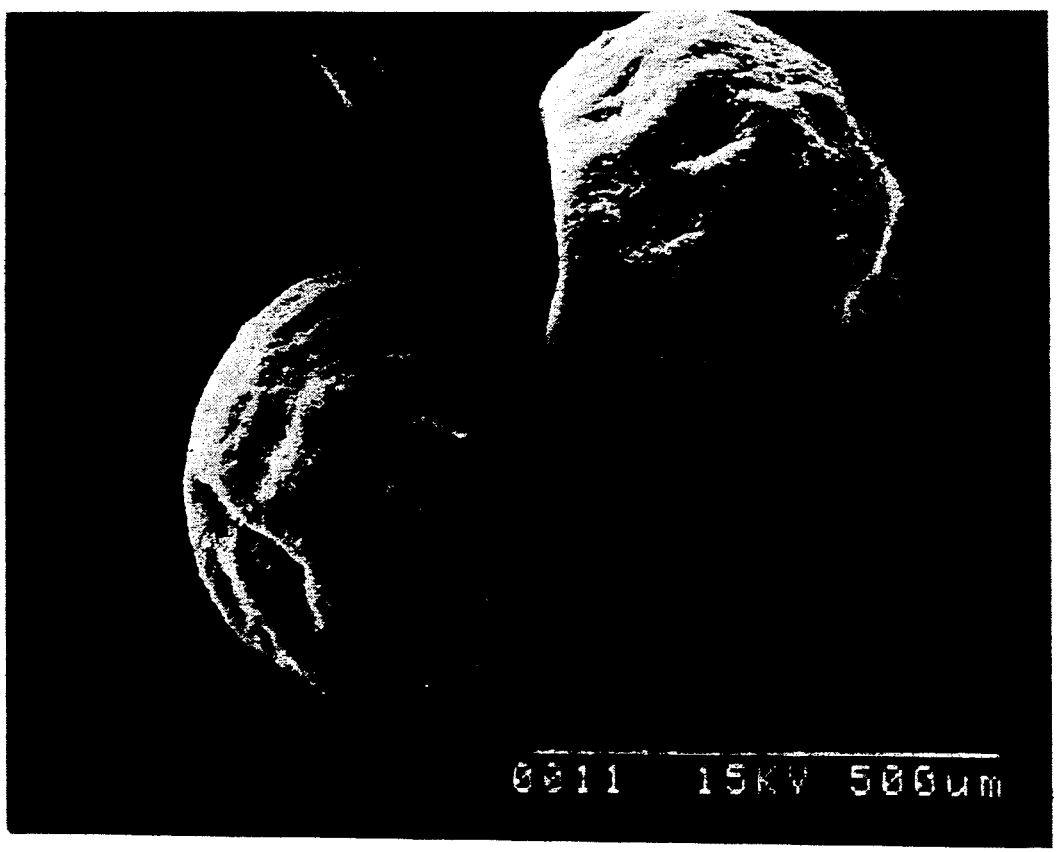
FIG. 1 Microcapsules, scanning electron microscopy. Note the irregular polyelectrolyte surface.

The subject invention provides a method of encapsulating viable tissue or cells within a double-walled bead comprising:

(a) suspending the tissue or cells in an aqueous medium which is physiologically compatible with the tissue and which contains a water soluble substance which
  (i) is physiologically compatible with the tissue; and
  (ii) can be gelled to form a bead;

(b) forming the suspension into droplets of a size sufficient to encapsulate the tissue or cells;

(c) treating the droplets so as to form discrete, shape-retaining temporary capsules;

(d) forming a permanent semipermeable membrane around the temporary capsules so as to obtain a single-walled bead encapsulating the tissue or cells; and (e) contacting the resulting single-walled bead with the water soluble substance under conditions such that a second membrane is formed so as to thereby obtain a double-walled bead encapsulating the tissue or cells.

In a preferred embodiment of the method, the tissue or cells comprise pancreatic islets. Individual cells, combinations of cells, whole islets of Langerhans, or or other tissue may be encapsulated.

The pancreatic islets may be from an animal distantly related or unrelated to the subject, such as a human being, who is the recipient of the microencapsulated donor islets.

The water soluble material of the method may be any water-soluble material which can be converted to a shape retaining mass. A preferred water soluble material is a water soluble, natural or synthetic polysaccharide gum such as an alkali metal alginate. A preferred gum is sodium alginate. Other gums which may be used in the subject method include guar gum, gum arabic, carageenan, pectin, tragacanth gum, xanthan gum or their acidic fractions.

In an embodiment of step (c) of the subject method, the droplets are subjected to a solution of multivalent cations, such as a calcium solution. The temporary capsules are gelled to form their shape by being exposed to a change in conditions such as being exposed to multivalent cations solution or to a pH change.

In one embodiment of step (d) of the method, a membrane is formed by subjecting the temporary capsules to polymer containing substituents reactive with the acid groups of the gum. The temporary capsules are hardened by polymers containing reactive groups such as amine or imine groups which react with acidic polysaccharide constituents. The polymer may be a polyamino acid, such as poly-l-lysine or polyethylenimine. In a preferred embodiment, the polymer is poly-l-lysine with a molecular weight ranging between about 18 Kd and 57 Kd, although the 18 Kd reagent is preferred since its use results in the smallest membrane porosity. Positively charged poly-l-lysine displaces calcium ions and binds negatively charged alginate, producing a polyelectrolyte membrane.

The subject invention further provides that prior to step (a) of the above-described method for producing double-walled beads or of a method for producing single-walled beads, the tissue or cells are treated so as to immunosuppress them. In a preferred embodiment, the treatment comprises ultraviolet-B irradiation of the tissue or cells. UV-B treated rat islets, which are then encapsulated and transplanted into NODs function much longer than non-UV-B treated, encapsulated islets, as shown in Experiment 3. There may be synergism of UV-B and microencapsulation. Furthermore, there may be synergism of recipient treatment with antibodies to helper T cells, and use of the protective microcapsule.

In another embodiment, the treatment comprises contacting the tissue or cells with cyclosporin.

The subject invention also provides a double-walled bead produced as a result of the above-described method. The double-walled bead, preferably of polylysine-alginate layering, is superior to single-walled beads because they will function for prolonged periods of time as opposed to single-walled beads. In addition, the above-described method for producing double-walled beads results in fewer deformed beads than the method for producing single-walled beads.

EXPERIMENT 1

Microcapsule Methodology

The technique of microencapsulation currently employed in several laboratories is adapted from the method originally reported by Lim and Sun (Lim, F. and A. Sun, Science 1980 210:908). The method utilizes alginate (beta-D-mannopyroanosyluronic acid and alpha-L-gulopyranosyluronic acid) in aqueous phase, under conditions which are physiological, with regard to pH and temperature. The technique devised in applicants' laboratory is modified from that of Darquy (Darquy, S. and G. Reach Diabetologia 1985 28:776) and Goosen (Goosen, M., et al., Biotechnol. Bioeng. 1985 27:146). Isolated islets are suspended 1:10 v/v in 1.7% sodium alginate in 0.9% saline, 10° C. Droplets containing islets in alginate are produced by extrusion (1.7 ml/min) through a 22 gauge air-jet needle (air flow 5 l/min). Droplets fall 2 cm into a 20 ml beaker containing 10 ml 1.1% $CaCl_2$ in 0.9% saline, pH 7.1 (all subsequent reagents used at room temperature (24°-27° C.). Negatively charged alginate droplets bind calcium and form a calcium-alginate gel. The gelled droplets are decanted and transferred to a 50 ml centrifuge tube, filled completely with 1.1% $CaCl_2$ for each 2–4 ml of microcapsules; and the tube is rotated gently, end over end, one revolution each 10 seconds, for 10 minutes. Microcapsules are allowed to settle; supernatant is aspirated; and then microcapsules are washed (for 15–20 seconds, that is, the time it takes to perform the manipulation) in 0.5% $CaCl_2$, followed by 0.28% $CaCl_2$ (in 0.9% saline, pH 7.1) (all washes use reagent volume to fill the centrifuge tube). After a final wash in 0.9% saline, poly-L-lysine, 0.5 mg/ml in saline is added (to fill the tube); and the tube is rotated for six minutes. Poly-L-lysine of m.w. ranging from 18,000 to 57,000 has been used in this formulation, although the 18,000 m.w. reagent is preferred, since its use results in the smallest membrane porosity (Goosen, M. et al., Biotechnol. Bioeng. 1985 27:146). Positively charged poly-L-lysine displaces calcium ions and binds negatively charged alginate, producing a polyelectrolyte membrane. After removal of poly-L-lysine, microcapsules are allowed to settle, and then are washed on 0.1% CHES in saline, pH 8.2, followed by another wash in 0.9% saline. Next, 0.17% sodium alginate is added, in a volume to fill the tube; and the microcapsules are rotated again for 4 minutes. Thereafter, alginate is aspirated and discarded, microcapsules are washed in 0.9% saline, and then additional poly-L-lysine (0.5 mg/ml in saline) is added (to fill the tube). Microcapsules are rotated for an additional six minutes, then washed again in 0.1% CHES (in 0.9% saline, pH 8.2), and then in saline, following which they are reincubated on the rotator, in dilute 0.17% sodium alginate for 4 min. Microcapsules then are washed in 0.9% saline, followed by addition of 55 mM sodium citrate in saline (to fill the tube), pH 7.4, in which the microcapsules are rotated for an additional 6 min. Sodium citrate solubilizes any calcium alginate which has not reacted with poly-L-lysine. Finally, microcapsules are washed 3 times in 0.9% saline, and then transferred to conventional tissue culture medium (DMEM plus 10% heat-inactivated fetal calf serum, pH 7.2), and stored in a servoregulated incubator, 90% air, 10% $CO_2$, at 22°-24° C.

Microcapsules formulated in this manner are translucent spheres, with diameters of 500–800 microns. An electron micrograph (courtesy Dr. Michael Marin) of microcapsules, shown in FIG. 1, reveals the surface characteristics of the polyelectrolyte membrane.

Functional and Morphologic Studies of Islets in Microcapsules

Figure 2:
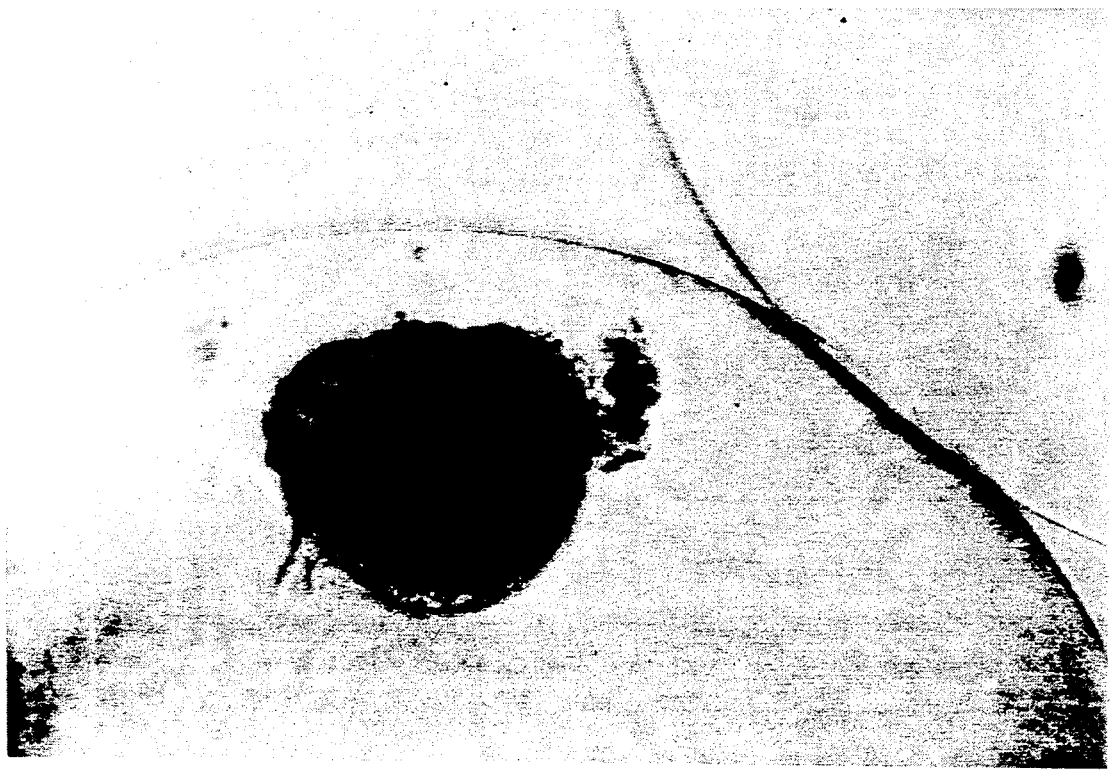
FIG. 2 Microencapsulated rat islet. Phase contrast microscopy, approximately 250×.
Figure 3A:
FIG. 3 (A) Isolated human islets, in culture. Phase contrast microscopy; approximately 250×. (B) Microencapsulated human islets; phase contrast microscopy; approximately 250×.
Figure 3B:
Figure 4:
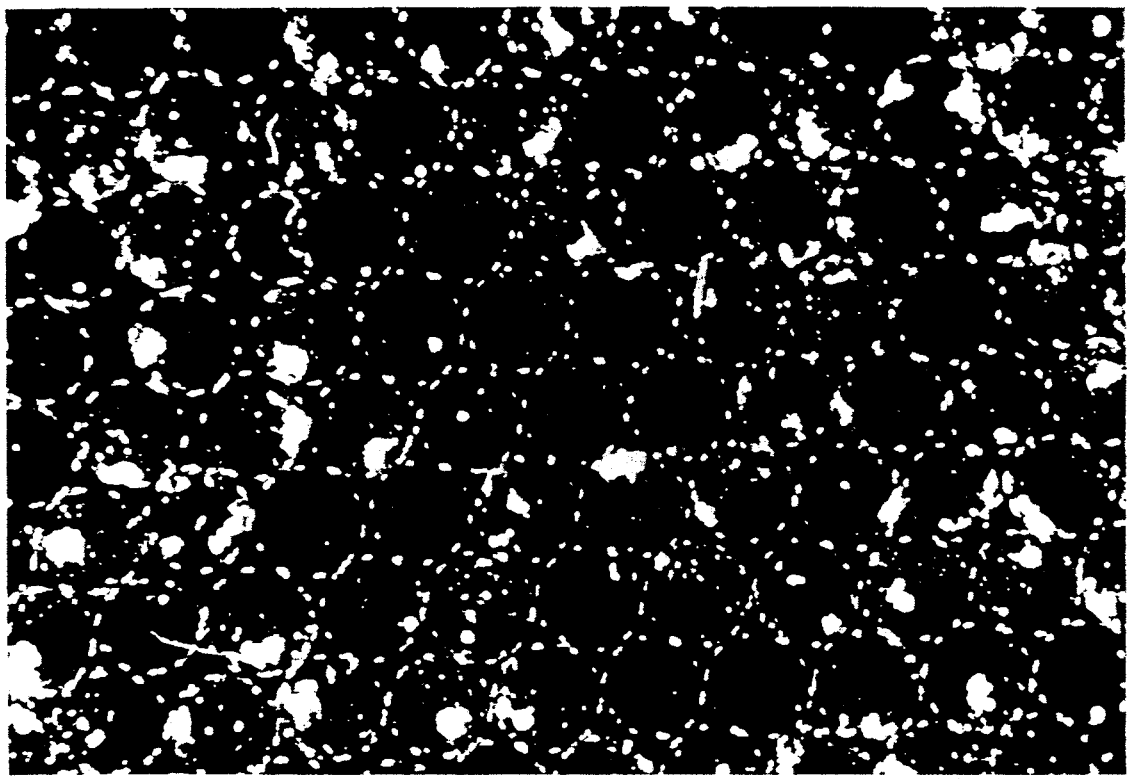
FIG. 4 Microcapsules containing rodent islets; note that not all microcapsules contain islets. Dark field microscopy; approximately 40×.

In a recent series of experiments in applicants' laboratory, human, rat and mouse islets have been isolated, using conventional collagenase digestion, differential ficoll centrifugation, as previously described (Weber, C. et al., Transplant Proc 1986 18:823; Chabot, J. et al., Transplant Proc. 1987 19:1160; Reemtsma, K. et al., In Friedman, E. and F. L'Esperance, Jr. eds. Diabetic Renal-Retinal Syndrome III, New York: Grune and Stratton 1986:521; Reemtsma, K. et al., 1987; In: J. Andrade, ed. Artificial Organs. Deerfield, Fla: VCH Publ., 1987:393). Phase contrast microscopy of microencapsulated human and rat islets (shown in FIGS. 2 and 3) reveals intact, viable islets, with apparent viable single islet cells as well, testifying to the delicacy of the encapsulation technique. Shown in FIG. 4, is a low-power dark-field microscopic view of encapsulated rodent islets. Note that not all microcapsules contain islets.

Glucose-stimulated insulin release from microencapsulated human, mouse and rat islets, detailed in Table 1, revealed both glucose and theophylline-stimulated insulin (Herbert, V. et al., 1965 J Clin Endocrinol 25:1375) release from encapsulated islets.

TABLE 1

Glucose-responsiveness of isolated, microencapsulated islets in vitro (sequential hourly incubations)

| | Media insulin ($\mu$U/h) Glucose | | | |
|---|---|---|---|---|
| | 50 mg/dl | 500 mg/dl | 500 mg/dl + 20 mM theophylline | 50 mg/dl |
| Human islets | | | | |
| 1 | 51 | 90 | 180 | 120 |
| 2 | 590 | 500 | 520 | 620 |
| 3 | — | 2575 | 2950 | — |
| Mouse islets | | | | |
| 1 | 170 | 480 | 860 | 620 |
| 2 | 140 | 380 | 700 | 490 |
| Rat islets | | | | |
| 1 | 520 | 680 | 1000 | 940 |

Using microencapsulated peripheral blood lymphocytes ($3-5 \times 10^6$) as stimulators in conventional, one way mixed lymphocyte reactions (MLR) (Meo, T. 1979 In Lefkovitz, I. and B. Pernis, eds. Immunological Methods. New York: Acad Press, 1979:227ff), applicants found that the stimulation index of MLRs with encapsulated stimulators was markedly reduced compared to control wells containing nonencapsulated stimulators. This was true for both human-human, monkey-monkey and cross-species reactivity as well (see Table 2).

TABLE 2

Mixed lymphocyte reactivity (standard vs. encapsulated lymphocytes)

| | | Human 1 | Human 2 | Human 3 | Human 4 | Monkey 1 | Monkey 2 |
|---|---|---|---|---|---|---|---|
| Human 1 | Std. | x | 11.06 | 17.20 | 24.27 | 17.70 | 27.37 |
| | Enc. | | 0.82 | 2.85 | 1.45 | 1.57 | 1.03 |
| Human 2 | Std. | 3.93 | x | 2.73 | 2.54 | 3.15 | 2.10 |
| | Enc. | 0.81 | | 5.71 | 1.80 | 1.72 | 5.51 |
| Human 3 | Std. | 18.49 | 6.14 | x | 10.98 | 5.81 | 10.97 |
| | Enc. | 0.49 | 0.43 | | 0.27 | 1.06 | 1.19 |
| Human 4 | Std. | 2.1 | 1.09 | 1.34 | x | 1.90 | 1.92 |
| | Enc. | 0.97 | 1.08 | 1.51 | | 3.48 | 1.50 |
| Monkey 1 | Std. | 13.05 | 29.46 | 14.40 | 16.82 | x | 0.44 |
| | Enc. | 6.77 | 3.62 | 6.92 | 4.93 | | 4.21 |
| Monkey 2 | Std. | 4.54 | 13.70 | 4.56 | 4.30 | 0.94 | x |
| | Enc. | 2.18 | 0.72 | 2.58 | 0.84 | 1.29 | |

Data expressed as stimulator indices.

Figure 5:
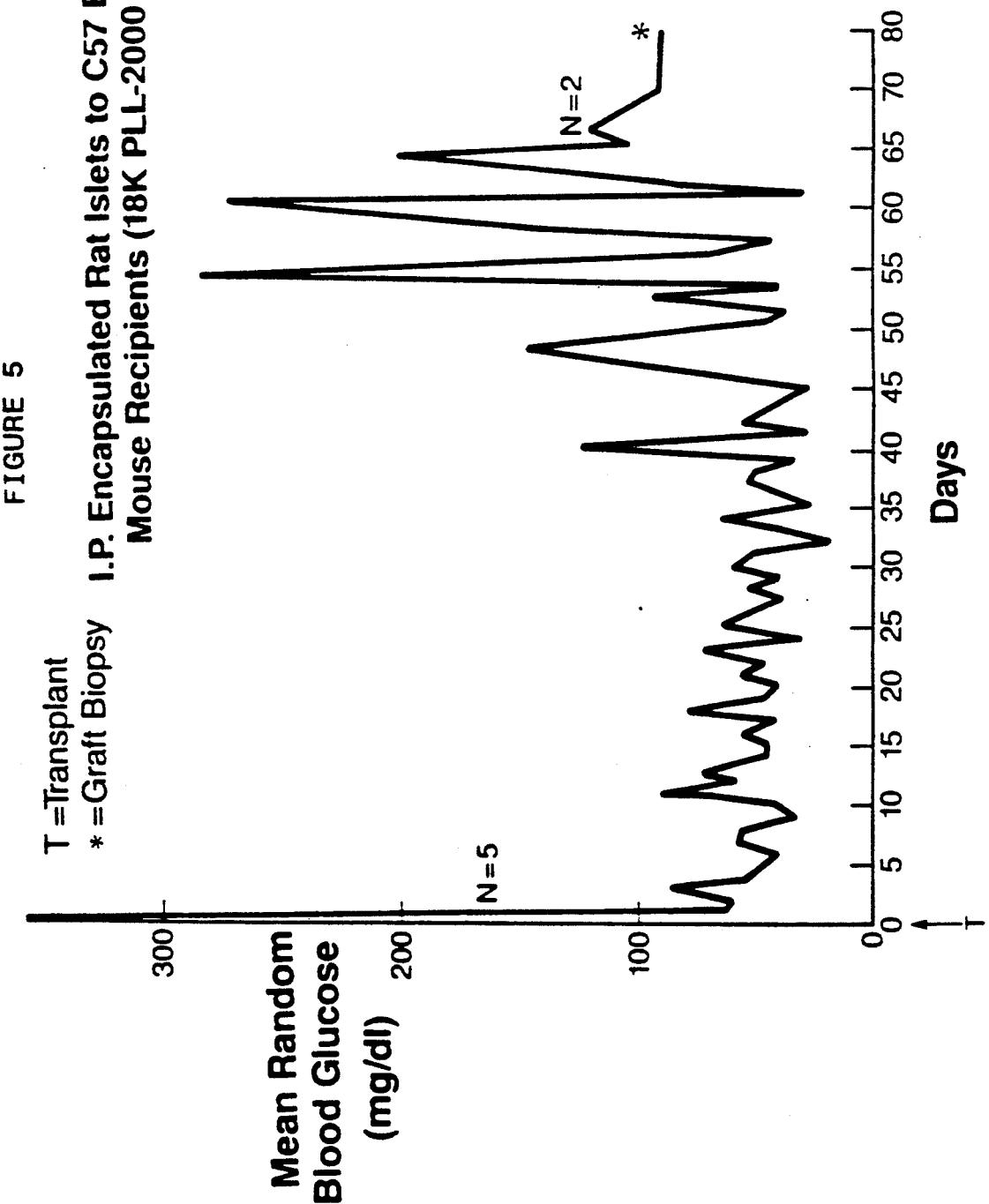
FIG. 5 Blood glucose following intraperitoneal xenotransplantation of microencapsulated rat islets into streptozotocin-diabetic mice.
Figure 6:
FIG. 6 Microencapsulated rat islet biopsied from recipient mouse after >80 days intraperitoneally. Note intact microcapsule, viable islet cells and lack of cellular reaction. Few cells seen are red blood cells, secondary to the biopsy procedure. Conventional light microscopy, H.&E.; approximately 400×.
Figure 7:
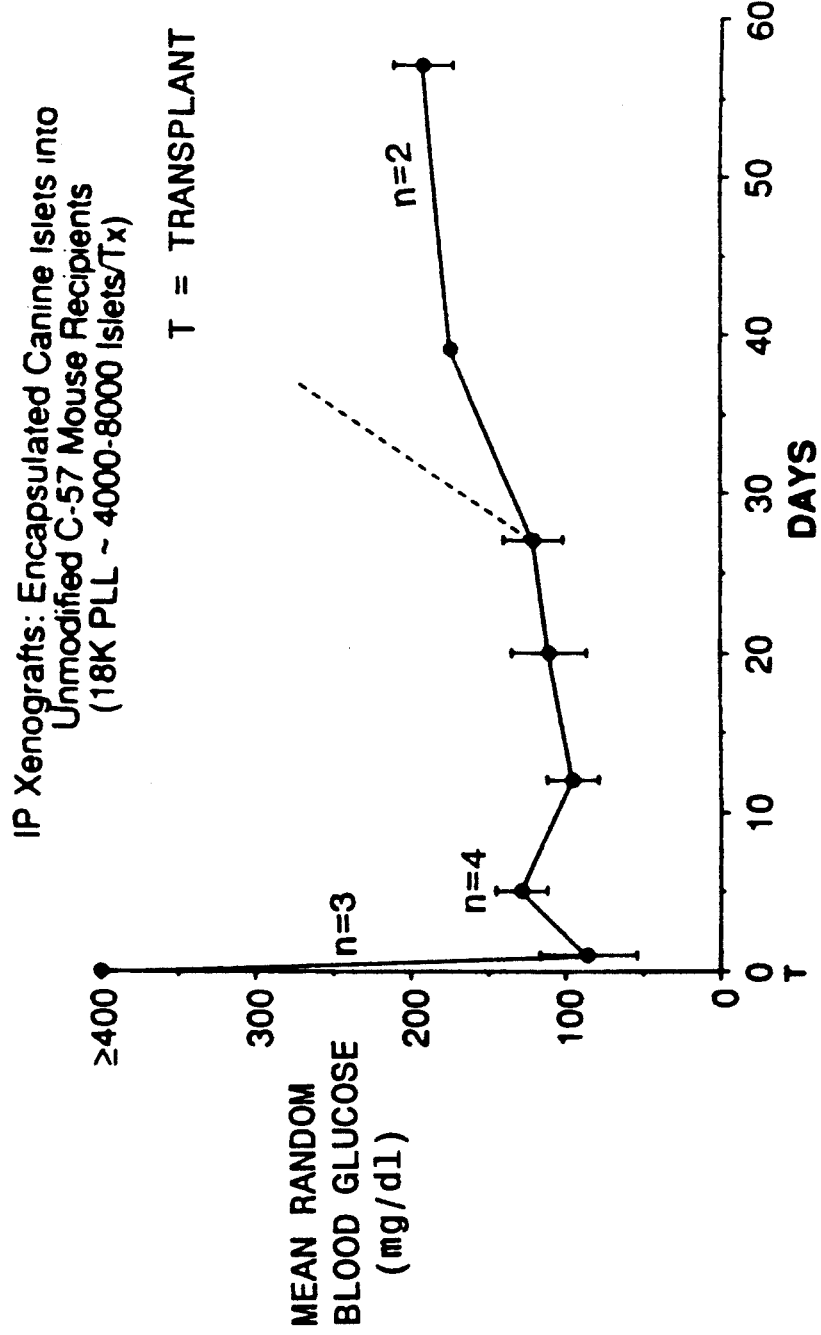
FIG. 7 Random blood glucose value ($\bar{x} \pm SEM$) following encapsulated canine islet xenotransplantation (i.p.) into SZN-diabetic C57BL/6J mice. Microcapsules produced with 18,000 m.w. poly-l-lysine (18K-PLL).

Xenotransplantation of 2000 microencapsulated donor Lewis rat islets intraperitoneally into streptozotocin-diabetic C57BL/6J mice (n=5) resulted in prompt normoglycemia in all recipients, within 24 h (see FIG. 5). Random blood glucose (Ente, G. et al., 1974 Am J Clin Pathol 61:612) determinations noted relative hypoglycemia (mean blood glucose=46±8 mg/dl) (day 5 post-transplant) in murine recipients of microencapsulated rat islets. Low-to-normal blood glucose levels were noted for up to 80+ days following xenotransplantation (no recipient immunosuppression). Biopsies of microcapsules from two recipient mice (>80 days) revealed intact microcapsules with viable rat islets within, and no cellular reaction around microcapsules (see FIG. 6). Implantation of empty microcapsules had no effect on blood glucose of diabetic mice (n=10).

Current studies, (Weber, C. et al., Transplantation 1990 49:396; see Experiment 2, infra) have revealed that microencapsulated canine islets (donor islets provided in collaboration, by Dr. Ray Rajotte) will normalize blood glucose of diabetic C57BL/6J mice for up to 70 days, without recipient immunosuppression.

Discussion

Microencapsulation is remarkably effective in preventing the destruction of xenogeneic donor islets in diabetic recipient mice. Applicants' data is consistent with those recently published by Ricker, et al. (Ricker, A. et al., 1986 In: M. Jaworski, ed. The Immunology of Diabetes Mellitus. Amsterdam: Elsevier 1986:193) and O'Shea (O'Shea, G. and A. Sun, Diabetes 1986 35:943). The finding in several laboratories that empty microcapsules evoke minimal reactions is of obvious importance for future studies in other animal models of diabetes, such as the NOD mouse and the BB rat.

The technique of microencapsulation is relatively nontoxic to donor islets, as evidenced by morphological and functional evaluations. The ability to construct a protective barrier without injury to individual islets is clearly advantageous.

Recent studies by Ricker (Ricker, A. et al. 1986 In: M. Jaworski, ed. The Immunology of Diabetes Mellitus. Amsterdam: Elsevier; and Ricker, A. et al. Cold Spring Harbor Symposium in Immunology of Diabetes, Abstracts, 1987), Calafiore (Calafiore, R. et al., Diabetes 1989 38(suppl.1):297; and Calafiore, R. et al. Clin Res 1987 35:499A), and in applicants' laboratory (Weber, C. et al., Transplantation 1990 49:396; see Experiment 2, infra) have suggested that spontaneously diabetic NOD mice destroy even microencapsulated donor islets, with an intense cellular reaction surrounding microcapsules within 10–14 days after transplantation. Current experiments in applicants' laboratory (Weber, C. et al. Transplantation 1990 49:396; see Experiment 2, infra) have suggested that helper T-lymphocytes are involved in this host reaction. These observations are important for future studies of the transplantation of xenografts of discordant islets into human diabetic patients.

EXPERIMENT 2

Introduction

Islet transplants for large numbers of patients with diabetes will require xenografts. Microencapsulation is an appealing method for islet xenografting. However, graft function has been limited by a cellular reaction, particularly intense in spontaneously diabetic, NOD mice. The purpose of this study was to elucidate the mechanism of this reaction. Poly-l-lysine-alginate microcapsules containing 4000–12,000 dog or 1800–2000 rat islets were xenografted intraperitoneally into streptozotocin (SZN)-diabetic C57BL/6J and NOD mice, with or without recipient treatment with GK 1.5 (anti-CD4 monoclonal antibody) (20–30 μl i.p. every 5 days, begun on day −7. Grafts were considered technically successful if random blood glucose (BG) was normalized (<150 mg/dl) within 36 hr. Graft failure was defined as BG>250 mg/dl. Dog and rat islets in microcapsules normalized BG in both SZN and NOD mice within 24 hr routinely. Empty microcapsules and GK 1.5 treatments alone did not affect BG. NODs destroyed both microencapsulated dog and rat islets more rapidly than did SZN-diabetic mice ($P<0.01$). Graft biopsies showed an intense cellular reaction, composed of lymphocytes, macrophages and giant cells, and no viable islets, GK 1.5 treatment significantly prolonged both dog-to-NOD and rat-to-NOD grafts ($P<0.01$). Biopsies of long-term functioning grafts (on days 65–85) demonstrated viable islets and no cellular reaction around microcapsules; 1.4 rat and ⅜ dog islet xenografts continued to function indefinitely in NOD recipients, even after cessation of GK 1.5 therapy. Prediabetic NODs receiving encapsulated dog or rat islets mounted a moderate cellular reaction to grafts. Empty microcapsules excited no cellular reaction in diabetic or prediabetic NODs. Applicants conclude that the NOD reaction to microencapsulated xenogeneic islets is helper T cell-dependent, and that the target of this reaction is not the microcapsule itself, but the donor cells within.

Models of Islet Transplantation in Diabetic Man: The Spontaneously Diabetic NOD Mouse Encouraging results with survival of islet xenografts in streptozotocin-diabetic mice prompted several recent studies of xenogeneic islets grafted into spontaneously diabetic nonobese diabetic (NOD) mice. Spontaneous diabetes in mice is perhaps the best available model of human type I diabetes. CD4+ and CD8+ lymphocyte insulitis precedes beta cell destruction (Sarmiento M., et al., J. Immunol 1980 125:2665). Cytotoxic T lymphocytes specific for beta cell antigen have been identified (Miller B, et al., J. Immunol 1988 140:52). Inhibition of macrophages (Haskins K., et al., Diabetes 1988 37:1444) or CD4+ helper T lymphocytes (Lee K., et al., Diabetes 1988 37:989 and Shizuru J. et al., Science 1988 240:659) prevents development of the disease.

Islet Allografts and Xenografts in Spontaneously Diabetic NOD Mice

Shiogama et al. (Shiogama T, et al., Cold Spring Harbor Symposium, October 1987:51A), Shizuru et al. (Shizuru J., et al., Cold Spring Harbor Symposium, October 1987:51A) and Wang et al. (Wang Y., et al., Transplantation 1988 46:101S; Wang Y., et al. Diabetes 1987 36:535) found that Islet allografts were promptly destroyed in unmodified NOD recipients, and that depletion of helper T lymphocytes with a short course of anti-CD4 monoclonal antibody (MoAb) resulted in prolonged (20 days), but not indefinite, islet allograft survival. Microencapsulated rat (Ricker A, et al., In Jaworski M., ed. The Immunology of Diabetes Mellitus. Amsterdam: Elsevier, 1986:1193) and dog (Wang Y., et al., Diabetes 1987; 36: 535) islet xenografts were destroyed in unmodified NODs within 5–7 days, with an intense cellular reaction surrounding the microcapsules (Ricker A, et al., supra) This "hyperimmune" reaction was delayed by dexamethasone (Calafiore R., et al., Clin Res 1987 35:499A) or oxygen free-radical scavenger (Wang Y., et al., Diabetes 1987; 36: 535) therapy of NOD recipients; however, indefinite survival of microencapsulated islet xenografts was not observed. Empty microencapsules elicited little or no reaction in NODs (Ricker A, et al., supra); and microencapsulated rat pheochromocytoma or hepatoma cells did elicit a cellular reaction, suggesting that the reaction in NODs was not directed against the microcapsule itself, but against a secreted product of the xenogeneic cells within.

Rationale For The Present Study

The purpose of this study was to elucidate the mechanism(s) responsible for the destruction of microencapsulated xenogeneic islets by NOD mice. Based upon the available data, applicants postulated that the reaction to microencapsulated islets in NODs was an immunologic one. Applicants chose to compare the reaction of SZN-diabetic with NOD mice, and applicants perturbed NOD T helper cell function by administering GK 1.5 MoAb. Applicants transplanted both dog and rat islets, to compare the immunologic reaction to concordant and discordant donor islets.

MATERIALS AND METHODS

Animals

Donors of islets were either young adult male Lewis rats (Microbiological Associates) or outbred mongrel dogs. Young adult male C57BL/6J mice were purchased from Jackson Laboratories, Bar Harbor, Me. Young adult male and female NOD mice were derived from a breeding colony nucleus originally provided by Dr. Yoshihiro Tochino, Osaka, Japan, to Merck, Sharp, and Dohme Research Laboratories. NODs used in current experiments were bred at Merck, Sharp, and Dohme, and transferred to Columbia University, where they were maintained under specific pathogen-free conditions. NODs older than 70 days were tested with Tes-tape (Eli Lilly) weekly for glycosuria, and were classified as diabetic on consistent demonstration of values of 1+ or higher, as previously described (Ricker A., et al., Cold Spring Harbor Symposium, October 1987:53A). NODs were treated with Lente pork insulin (Eli Lilly) (2–4 U/day) prior to transplantation. C57BL/6J mice were made diabetic by administration of streptozotocin (SZN) (Upjohn) 220 mg/kg i.p., in citrate buffer, pH=4.0. As previously described (Weber, C., et al., Transplant Proc. 1986 18:823), C57BL/6J mice were classified as diabetic when at least three tail vein random blood glucose (Ente G., et al., Am J Clin Pathol 1974 61:612) determinations, measured over at least 21 days, were >400 mg/dl.

Donor Islet Isolation

Rat islets were isolated by duct distension, collagenase digestion, and density gradient ficoll centrifugation, as previously described (Weber, C., et al., Transplant Proc. 1986 18:823). Dog islets were isolated by collagenase duct injection, followed by density gradient centrifugation, as previously described (Warnock G. and Rajotte R., Diabetes 1988 37:467). Donor islets were maintained in conventional Petri dish tissue culture, as previously described (Weber, C., et al., supra and Chabot J., Transplant Proc. 1987 19:1160) in DMEM, plus 10% FCS, in a servoregulated air/$CO_2$ (90%/10%) incubator, 24° C. for periods of 1-5 days prior to microencapsulated and transplantation. In the case of dog islets, individual preparations of 20,000-70,000 islets were shipped overnight by air carrier in centrifuge tubes in complete medium, at room temperature.

Microencapsulation

The technique of microencapsulation developed in applicants' laboratory was modified from that reported by Reach (Darquy S. and Reach G., Diabetologia 1985 28:776) and has been published in detail (Weber C., et al., In Hardy, M., ed. Xenograft/25. Amsterdam: Elsevier, 1989). Briefly, islets were suspended in 1.5% sodium alginate in saline. Droplets containing islets in alginate were produced by extrusion through a 22 gauge air-jet needle with droplets allowed to fall into a beaker containing 1.1% $CaCl_2$. (Negatively charged alginate droplets bind calcium and form a calcium-alginate gel). Gelled droplets were decanted and transferred to a centrifuge tube containing 1.1% $CaCl_2$; and the tube was rotated gently for 10 minutes. Microcapsules were allowed to settle, and supernatant was discarded. Thereafter, with a series of washes, microcapsules were exposed to 0.55% and then 0.28% $CaCl_2$, followed by 0.5 mg/ml of 18,000 m.w. poly-l-lysine, with rotation in a centrifuge tube again, for six minutes. After incubation with poly-l-lysine, capsules were washed in 0.1% CHES, followed by an additional wash with 0.15% sodium alginate, and then a saline wash. Thereafter, 55 mM sodium citrate was added for 6 minutes; and then microcapsules were washed in saline and transferred to conventional tissue culture Petri dishes, as described above.

Monoclonal Antibody Preparation and Studies

The anti-L3T4 antibody (GK 1.5) (Dialynas D., et al., J. Immunol 1983 131:2445) (TIB 207, ATCC) used in vivo was precipitated from ascites fluid grown in outbred nude mice (Charles River Breeding Lab., Wilmington, Mass.) with 50% ammonium sulfate. The precipitate was dissolved and dialyzed into 0.1M $NaHCO_3$ containing 0.15M NaCl. Mice received intraperitoneal doses of 20-30 μl (approximately 100 μg) of anti-L3T4 antibody diluted in 0.2 ml of sterile PBS every 5 days, beginning 5-14 days prior to transplantation. Previous studies with this regimen have shown that, by fluorescence-activated cell sorter measurements, in NOD mice receiving two injections of anti-L3T4 antibody, >95% of splenic L3T4 cells were eliminated (Ricker A., et al., Cold Spring Harbor Symposium, October 1987:53A).

To monitor in vivo efficacy of GK 1.5 treatments, peripheral blood of selected NOD mice was subjected to analysis by FACS (FACS IV, Becton Dickinson, Mountainview, Calif.), after incubation with anti-L3T4 supernatant plus FITC-antiratkappa (MAR 18.5, Becton Dickinson) (Ricker A., et al., Cold Spring Harbor Symposium, October 1987:53A).

Implantation and Graft Biopsy Procedures

At the time of xenotransplantation, microcapsules were transferred gently from culture dishes to centrifuge tubes, washed once in Hanks' balanced salt solution, and then transferred with conventional clinical intravenous tubing to a syringe, maintaining sterile conditions. Recipient mice were anesthetized with metafane inhalation; and a 0.3-cm midline celiotomy was made, through which the microcapsules were introduced into the free peritoneal cavity. Two-layer closure of the incision was done with absorbable suture. Control mice received empty microcapsules i.p., nonencapsulated donor islets i.p., or nonencapsulated donor islets injected into the spleen, as previously described (Weber, C., et al., Transplant Proc 1986 18:823). Tail vein blood glucose was monitored daily for 14 days, and then biweekly, as indicated. Biopsies of grafted microcapsules and of donor pancreas were done with metafane anesthesia, which allowed survival of NODs with long-term-functioning grafts.

Graft and pancreas biopsies were fixed in Bouin's solution and processed for paraffin sectioning. Tissue sections (4 μm) were stained with hematoxylin and eosin; and the presence of insulin in donor islets was determined using immunoperoxidase histochemistry (Warnke R and Levy R., J. Histochem Cytochem 1980 28:771).

Results

Figure 11:
FIG. 11 Representative biopsy of viable encapsulated rat islet retrieved from peritoneal cavity of unmodified SZN-diabetic C57BL/6J mouse, 90 days after xenotransplantation. (see also FIG. 3.) (H&E; original magnification: ×400); note absence of cellular infiltrate at capsule wall (left).
Figure 12:
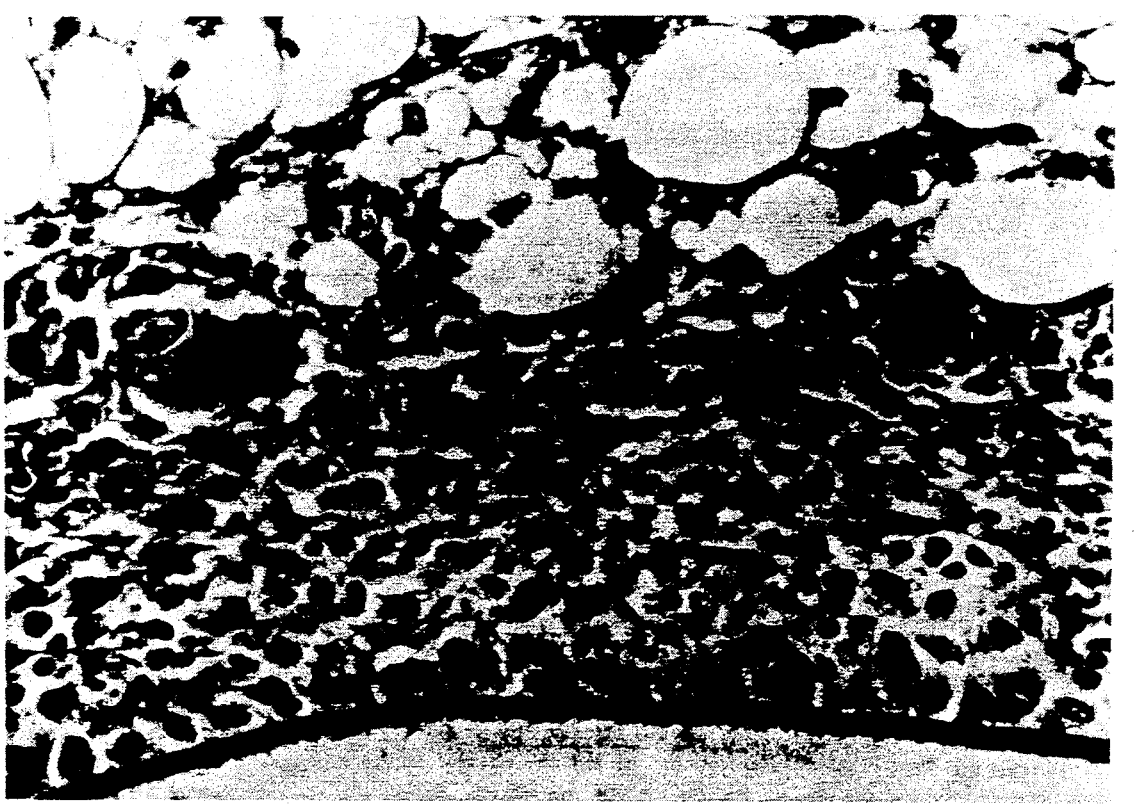
FIG. 12 Cellular reaction to microencapsulated dog islets; biopsy of i.p. xenograft from unmodified NOD mouse (see also FIG. 8), on day 7. Dark like is capsule wall (H&E; original magnification: ×400).
Figure 13:
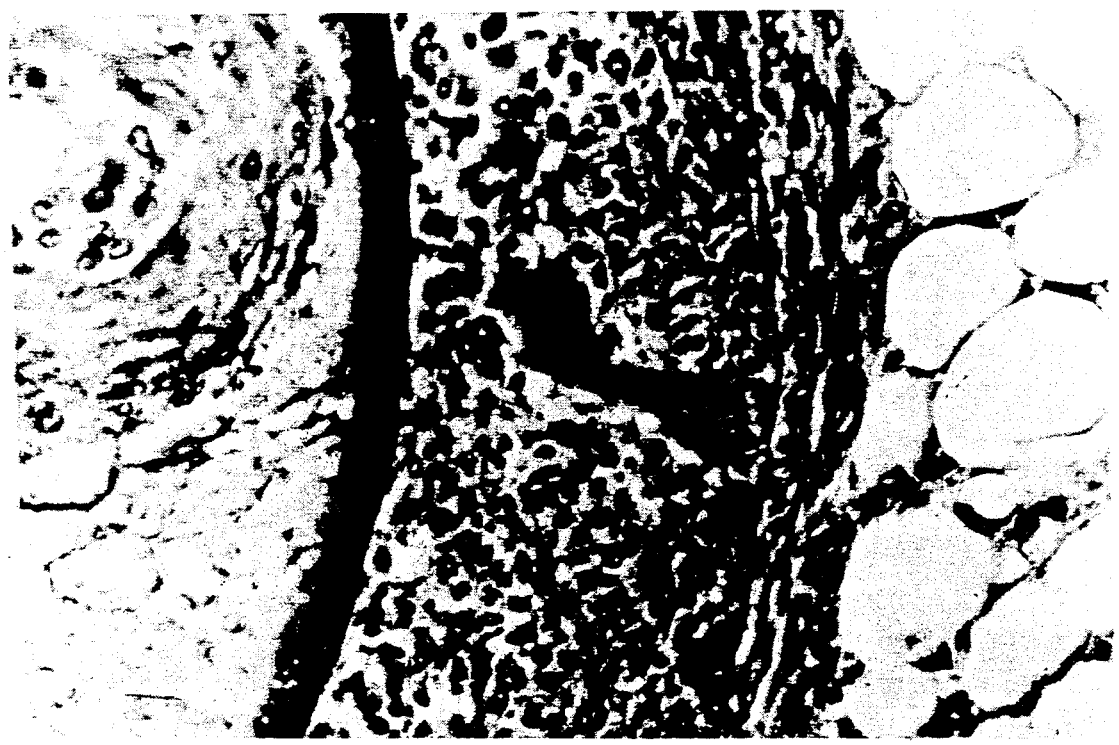
FIG. 13 Cellular reaction to microcapsule containing rat islets; biopsy of i.p. xenograft from unmodified NOD mouse (see also FIG. 10), on day 7 before transplantation (H&E; original magnification: ×360). Capsule wall on left; ischemic islet within capsule. Note multinucleate giant cell in infiltrate.

Dog and rat islets in microcapsules routinely normalized randon BG in both SZN and NOD mice within 24 hours after transplantation (Table 3, FIGS. 7-10). Empty microcapsules (n=6) did not affect blood glucose (Table 3, FIG. 9). Long-term functional survival was observed for 3/6 rat-to-C57BL/6J and 2/4 dog-to-C57BL/6J microencapsulated islet xenografts. Biopsies of these long-term-normoglycemic SZN recipients demonstrated viable donor islets and minimal cellular reaction around microcapsules (FIG. 11). As shown in FIGS. 8 and 10, NODs destroyed both dog and rat islets more rapidly than did C57 mice (P<0.01) (Table 3). NOD graft biopsies, on days 5-22 after xenotransplantation, showed an intense cellular reaction composed of lymphocytes, macrophages and giant cells, and no viable islets (FIGS. 12 [dog] and 13 [rat]) islets in unmodified NODs. This reaction was clearly different from the insulitis seen in the hose NOD pancreas.

Figure 14:
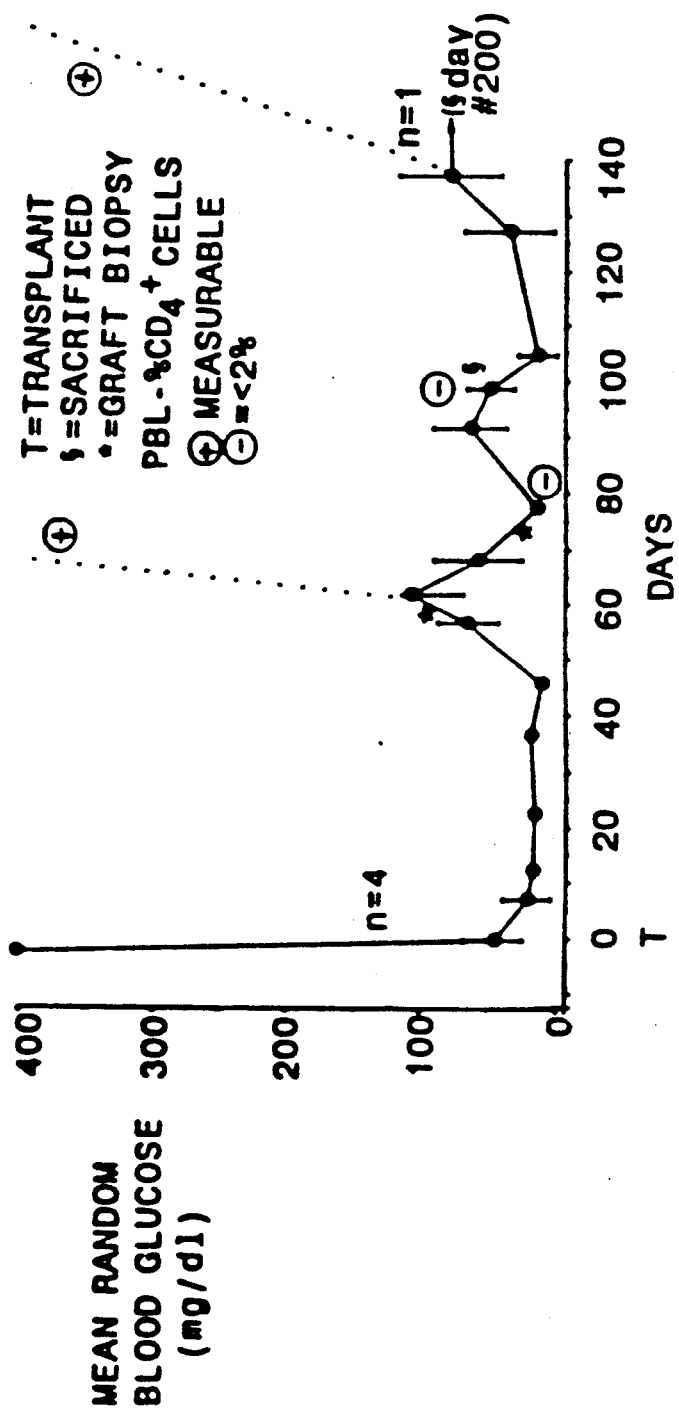
FIG. 14 Intraperitoneal xenografts of encapsulated rat islets into NOD mice treated with anti-$L_3T_4$ MoAB. Peripheral blood lymphocytes (—)% CD4+ cells measured by FACS analysis. Dashed lines denote individual graft failures.
Figure 15:
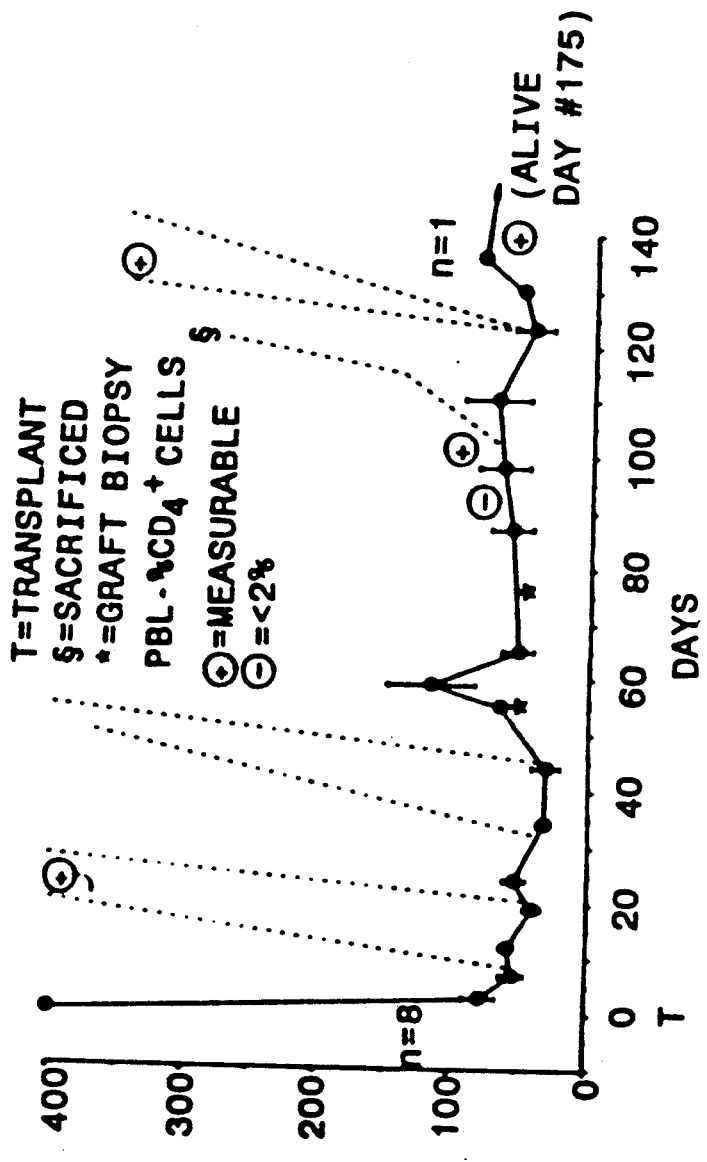
FIG. 15 Intraperitoneal xenografts of encapsulated canine islets into NOD mice treated with anti-$L_3T_4$ MoAB. Peripheral blood lymphocytes (—)% CD4+ cells measured by FACS analysis. Dashed lines denote individual graft failures.
Figure 16:
FIG. 16 Viable donor rat islet within intact microcapsule, biopsied from peritoneal cavity of anti-$L_3T_4$ MoAB-treated NOD mouse, day 80, following xenotransplantation. (see FIG. 17). Note absence of pericapsular infiltrate (H&E; original magnification: ×160).
Figure 17:
FIG. 17 Same histologic block as FIG. 10, adjacent section; immunoperoxidase stain for insulin, revealing multiple viable, insulin-containing beta cells; Day 80 following xenotransplantation. (original magnification: ×400).
Figure 18:
FIG. 18 Viable donor canine islet within intact microcapsule biopsied from peritoneal cavity of anti-$L_3T_4$-treated NOD mouse (see FIG. 15), day 80 following xenotransplantation. Note absence of pericapsular infiltrate (H&E; original magnification: ×400).
Figure 19:
FIG. 19 Same histologic block as FIG. 18, adjacent section, immunoperoxidase stain for insulin, revealing multiple, viable, insulin-containing donor dog beta cells; day 80, after xenotransplantation. (magnification: ×400).

GK 1.5 MoAb therapy significantly prolonged rat-to-NOD and dog-to-NOD islet grafts (FIGS. 14 and 15). Graft biopsies on days 65-85 demonstrated viable dog and rat islets and no perimicrocapsule cellular reaction in all four long-term NODs biopsied (FIGS. 16-19).

Antibody treatments were stopped after day 95 in all long-term-functioning NOD recipients. Eventual graft failure was observed for ½ recipients of rat islets and ¾ recipients of dog islets in microcapsules.

Figure 20A:
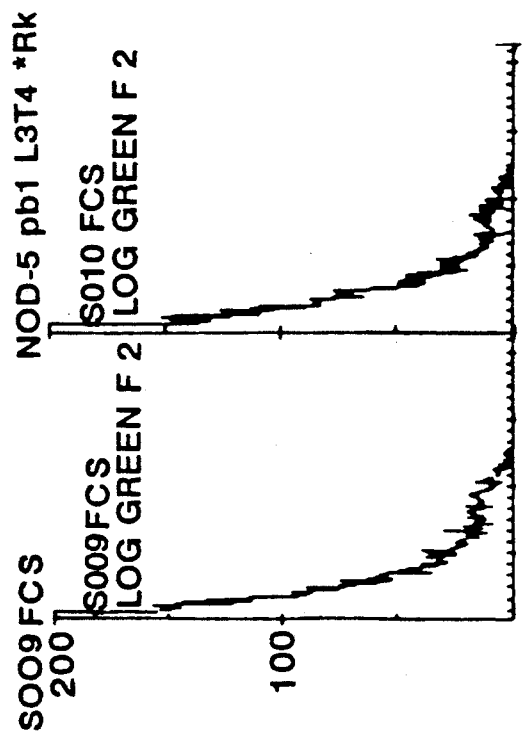
FIG. 20 FACS analyses of peripheral blood lymphocytes from (A) a NOD mouse treated with GK1.5, showing absence of helper T cells (left panel) and (B) a NOD mouse with detectable helper T cells (left panel). Right panels are FITC-antirat-kappa controls.
Figure 20B:
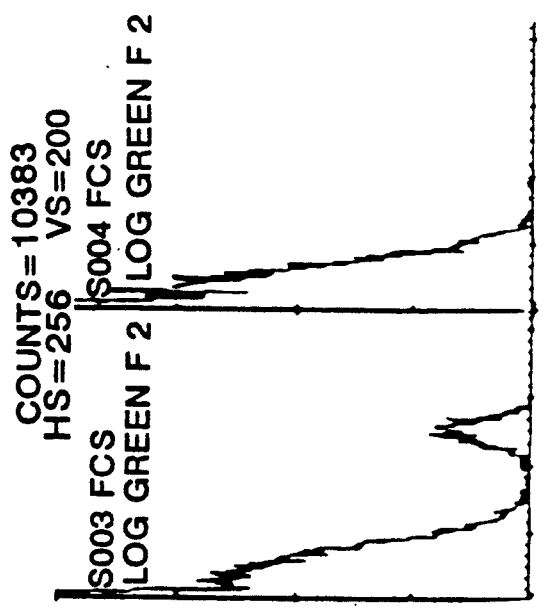

Flow cytometry (Miller, B., et al. J Immunol 1988 140:52) (FIG. 20) showed undetectable CD4+ cells in peripheral blood in all GK 1.5-treated NOD mice with functioning xenografts, when analyzed either early or late after transplantation, with one exception (FIG. 20), a NOD recipient of encapsulated dog islets, in the peripheral blood of which CD4+ cells were detectable on day 150, while the discordant islet graft was still functional.

Grafts of microencapsulated dog and rat islets that failed early (<60 days) despite anti-CD4 MoAb therapy, had measurable peripheral CD4+ cells in all cases.

Figure 21:
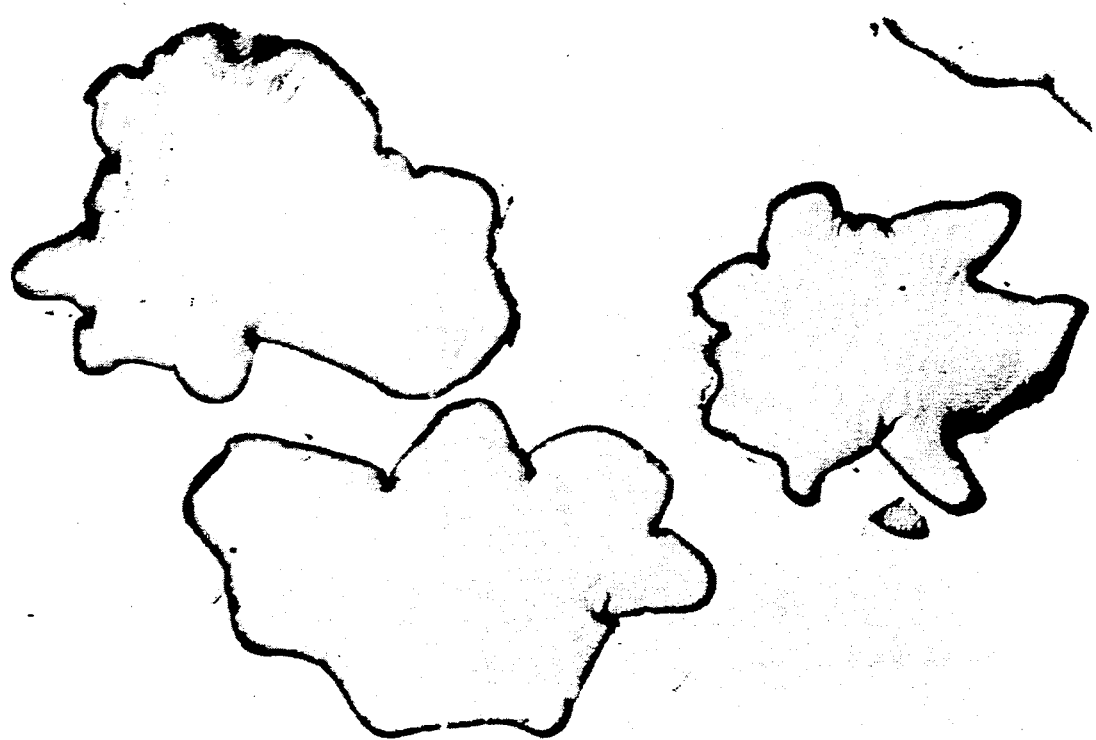
FIG. 21 Empty microcapsules, biopsied 14 days after intraperitoneal implantation into unmodified diabetic NOD mouse. Note absence of cellular reaction (H&E; original magnification: ×63).
Figure 22:
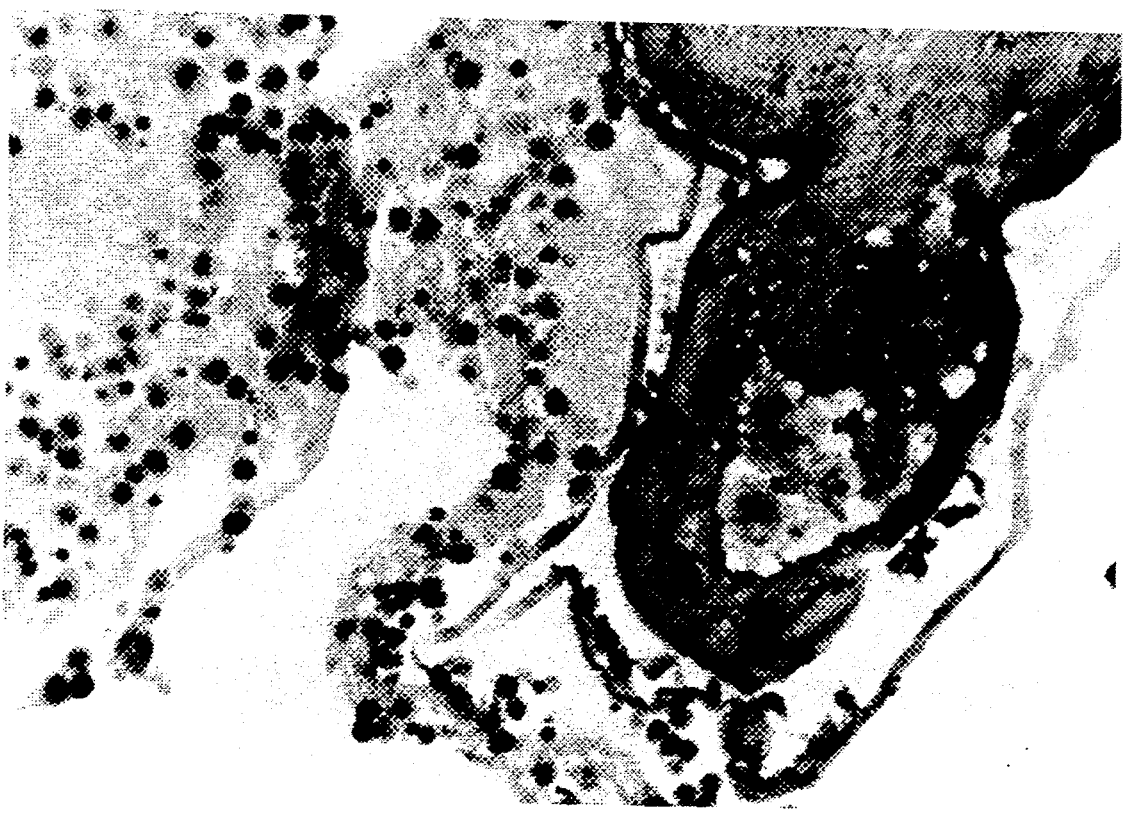
FIG. 22 UV-treated, microencapsulated rat islets, biopsied on day #28 (at rejection) from the peritoneum of a NOD recipient. H&E; orig. mag. approx. ×400. Note limited cellular reaction to graft.
Figure 23:
FIG. 23 Empty capsules, biopsied from peritoneal cavity of NOD mouse, day #185. H&E; orig. mag. approx. ×63. Note absence of cellular reaction.
Figure 24:
FIG. 24 UV-treated rat islets, in microcapsules, biopsied on day #136 (at rejection), from NOD mouse. H&E; orig. mag. approx. ×400. Note absence of cellular host reaction to this intraperitoneal xenograft.
Figure 25:
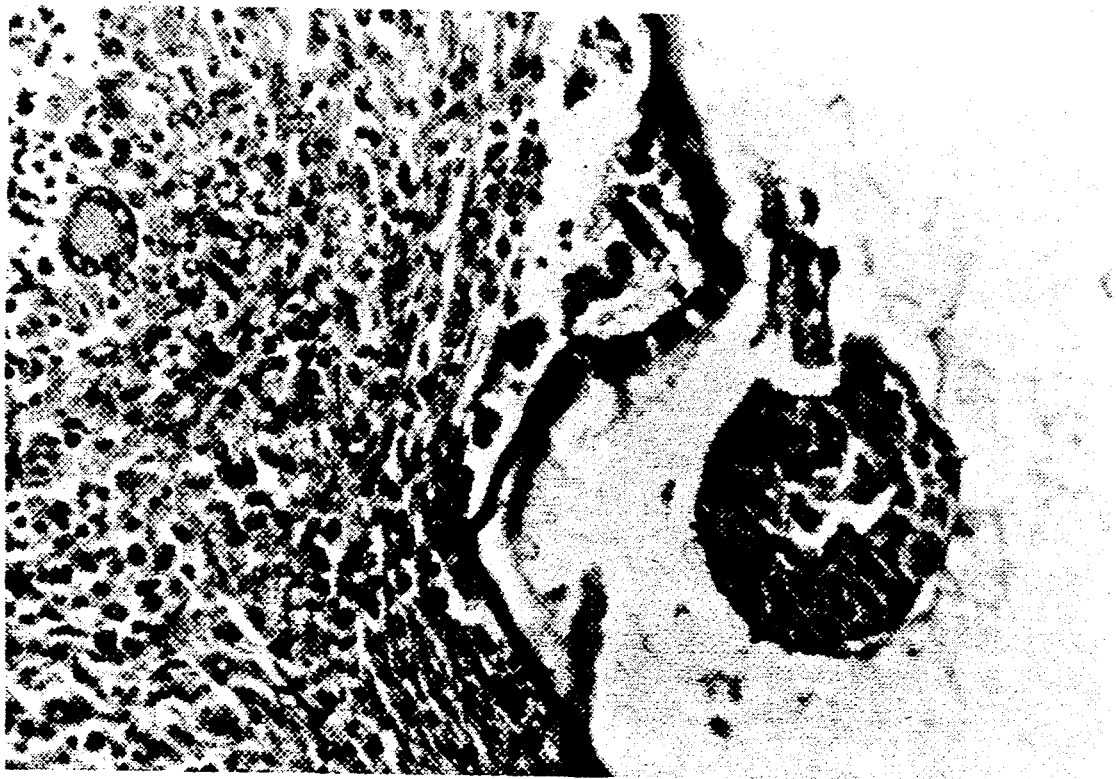
FIG. 25 Unmodified, microencapsulated rat islet, biopsied on day #10 (4 days post-rejection) from the peritoneum of a NOD recipient. H&E; orig. mag. approx. ×360. Note extraordinary cellular reaction around microcapsule.
Figure 26:
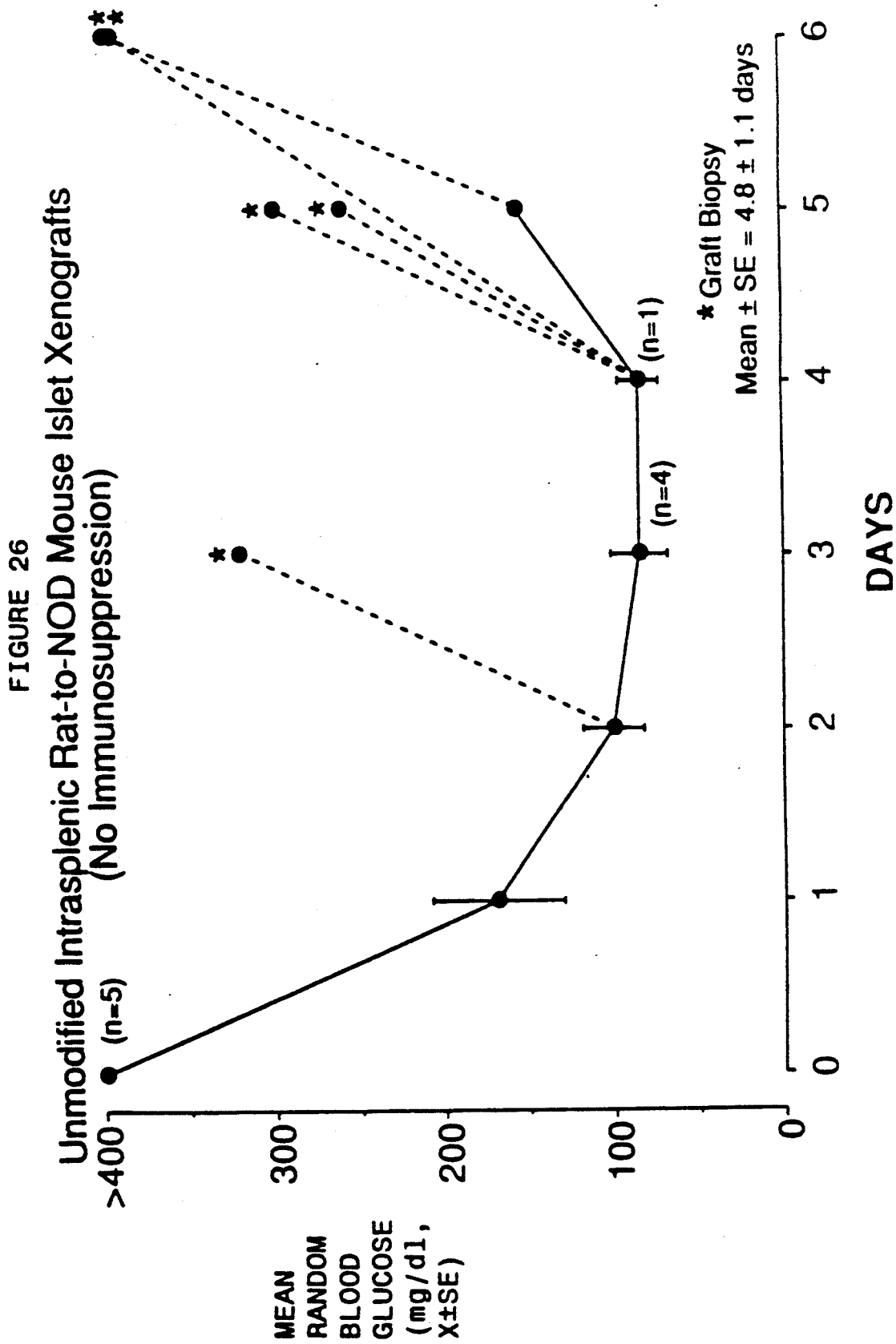
FIG. 26 Unmodified intrasplenic rat-to-NOD mouse islet xenografts (no immunosuppression).
Figure 27:
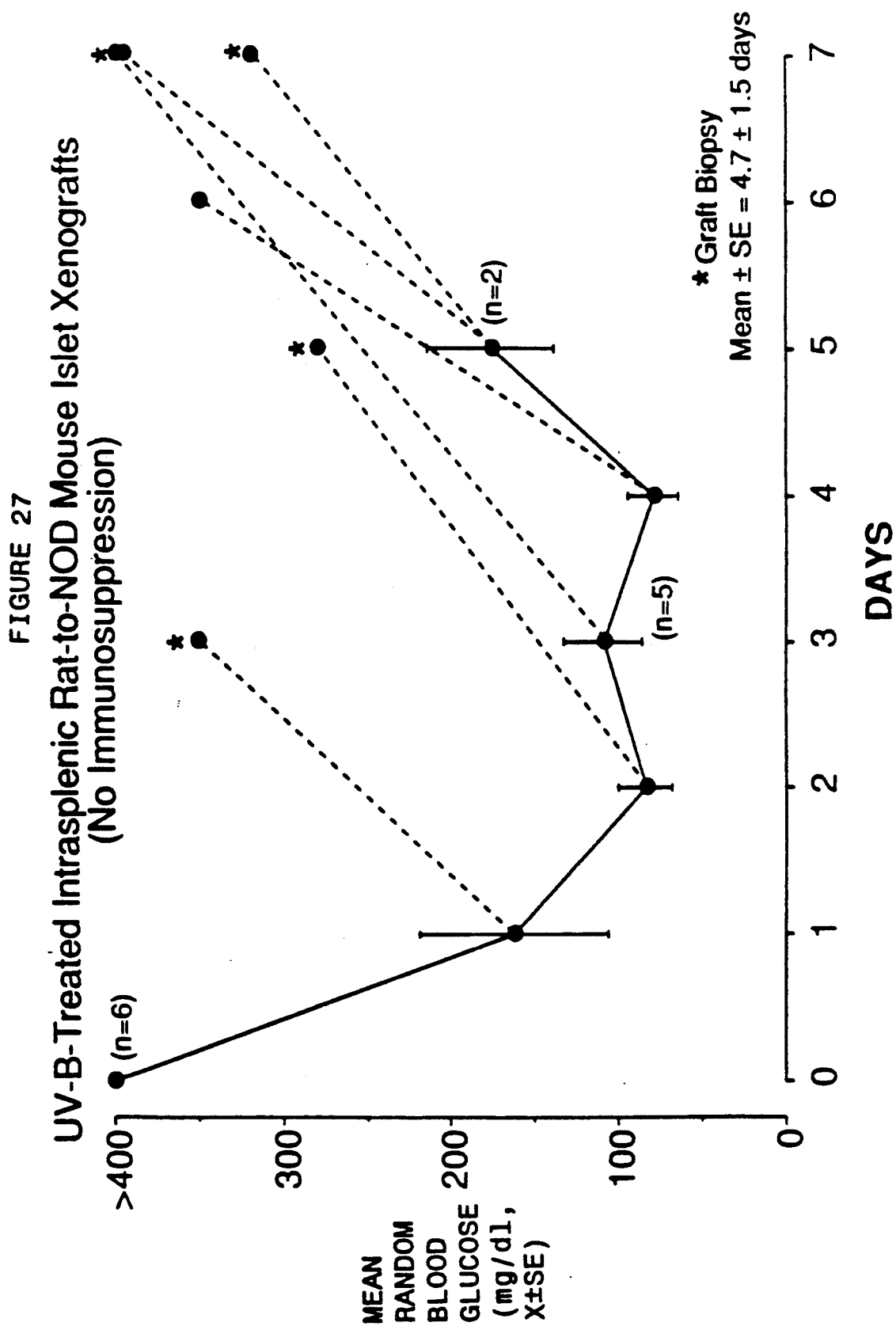
FIG. 27 UV-B treated intrasplenic rat-to-NOD mouse islet xenografts (no immunosuppression).

Empty microcapsules (n=4) excited no reaction in NODs (FIG. 21), confirming the studies of Ricker (Ricker A., et al., In jaworski M., ed. The Immunology of Diabetes Mellitus. Amsterdam: Elsevier, 1986:1193). Dog islets (12,000) xenografted into the spleen of unmodified NODs (n=3) failed to function, even on day 1 (Table 3), confirming the findings of graft nonfunction NODs noted by Wang et al. (Wang Y., et al. Diabetes 1987 36:535). Dog islets (12,000) xenografted intraperitoneally, without microcapsule protection, into anti-CD4 treated NODs resulted in fluctuating reductions of blood glucose for up to 28 days (n=2) (Table 3).

diabetic NODs, it may in fact be directed primarily toward xenogeneic, as opposed to islet, antigens.

Applicants believe that the data summarized above are extremely promising for the future of islet xenografts in humans, because the microcapsules themselves are biocompatible, and indefinite survival of both concordant (rat) and discordant (dog) islets in NOD mice can be achieved with combined use of microcapsules and selective inhibition of host helper T cells. Applicants think that it is relevant to human diabetes to pursue further studies of microencapsulated islet xenografts in spontaneously diabetic NOD mice, since this model of human diabetes is the best one available and the results of future studies may be clinically useful in treatment of human diabetics.

The antigen that is the target of the immunologic reaction toward microencapsulated islets remains elu-

TABLE 3

| Donor | Recipient | n | $Ab^a$ | $M^b$ | Functional graft survival Graft function (days) | (x ± SE [days]) | $BG,^c$ day 5 |
|---|---|---|---|---|---|---|---|
| Rat | SZN | 5 | — | + | 30, >100, >100, >100, >100 | 100 | 46 ± 8 (mg/dl) |
| Rat | NOD | 7 | — | + | 6, 7, 7, 8, 11, 15, 17 | $10 ± 2^d$ | 36 ± 8 |
| Rat | NOD | 4 | + | + | $200,^e 148,^e 97,$ 65 | $127 ± 30^f$ | 21 ± 5 |
| Dog | SZN | 4 | — | + | 36, 39, 61, 68 | 51 ± 8 | 82 ± 12 |
| Dog | NOD | 4 | — | + | 5, 7, 17, 17 | $11.5 ± 3^d$ | 66 ± 15 |
| Dog | NOD | 8 | + | + | 13, 26, 40, 50, 114, $121,^e$ $124,^e$ $175^g$ | $83 ± 21^h$ | 54 ± 9 |
| Dog | NOD | 2 | + | — | 24, 28 | 26 ± 2 | 167 ± 57 |
| None | SZN | 6 | — | + | 0, 0, 0, 0, 0, 0 |  | 354 ± 6 |
| Dog | NOD (splenic capsule) | 2 | — | — | 0, 0 |  | >400 |

$^a$Antibody (Ab) stopped at day 95.
$^b$M: microcapsules.
$^c$BG: random blood glucose.
$^d$P<0.02 vs rat → NOD w/o Ab.
$^e$Insulin-positive islets in microcapsules at biopsy (days 60-85).
$^f$P<0.02 vs rat → NOD w/o Ab.
$^g$Graft still functional.
$^h$P<0.02 vs. dog → NOD w/o Ab.

Dog islets in microcapsules provoked a focal and minimal cellular reaction in young, prediabetic NODs (n=4) grafted on day 30 after birth and biopsied 12-14 days later. Occasional viable donor islets were seen in capsules. Recipient pancreas biopsies showed scant lymphocytic infiltration. Microencapsulated rat islets, grafted into (older) 100-day-old prediabetic NODs and biopsied 60-70 days later, showed mild pancreatic insulitis, clearly evident pericapsule infiltrates, and no viable donor islets.

Discussion

From these studies, applicants have concluded that the reaction to microencapsulated xenogeneic rat and dog islets in diabetic NOD mice is helper T cell-dependent, and that the target of this reaction is not the microcapsule itself, but the donor cells within it. Enhanced survival of microencapsulated dog islets in NODs given anti-CD4 MoAb, compared with those xenografted into unmodified NODs and compared with the short-term survival of nonencapsulated islets xenografted into unmodified and into anti-CD4-treated NODs suggests that the effects of the microcapsule and MoAb therapy are synergistic. In addition, the presence of modest focal, but clearly identifiable, cellular infiltrates around microcapsules containing dog islets biopsied from very young (4-week-old) prediabetic NOD mice suggested that, although the reaction is accentuated in overtly sive. Although applicants' data may be interpreted to support the hypothesis that the antigen is a xenoantigen rather than an islet antigen, it must be noted that Shizuru et al. (Shizuru J. et al., Cold Spring Harbor Symposium, October 1987:51A), Mandel et al. (Mandel T., et al., Cold Spring Harbor Symposium, October 1987:52A) and Clare-Salzler et al. (Clare-Salzler M., et al., Cold Spring Harbor Symposium, October 1987: 52A) have reported that unencapsulated prediabetic NOD islets isografted into unmodified diabetic NOD recipients are rapidly destroyed, and that this reaction is not prevented by cyclosporine (Clare-Salzler M., et al., Cold Spring Harbor Symposium, October 1987:52A).

Equally unclear presently is the question of which subset(s) of helper T cells are critical to the antimicroencapsulated islet reaction. Recent studies from several laboratories using murine T cell clones have shown that CD4+ cells can be divided into two subsets, based upon lymphokine synthesis (Mosmann T., et al., J Immunol 1986 136:2348; and DeKruyff R., et al., J Immunol 1989 142:2575). Th1 helper T cells, via gamma interferon and IL-2, are responsible for activation of CD8+ cells, NK cells, and macrophages. Th2 helper T cells, via IL-4 and IL-5, are responsible for activation of B lymphocytes. In addition, it has been suggested that Th1 cells generate delayed-type hypersensitivity responses (Cher D. and Mosmann R., J Immunol 1987 138:3688).

Conventional light microscopic examinations of histologic sections of biopsied microcapsules at the time of rejection (described above) have shown the presence of macrophages, multinucleate giant cells, granulocytes, and lymphocytes consistent with an inflammatory reaction. Therefore, it is likely that the reaction to xenogeneic islets in microcapsules is IL-2-dependent.

Applicants' data, showing dependence of microencapsulated islet xenograft survival upon depletion of recipient NOD helper T cells does not resolve the question of whether helper T cells are directly toxic to encapsulated islets, or whether they act via recruitment of CD8+ T cells and/or other cells. A variety of studies of xenograft rejection have found evidence of actions of CD8+ cells on target donor cells (Lake S., et al., Diabetes 1989 38:244). In addition, it has been shown that both $CD4_+$ and $CD8_+$ cells are required for the transfer of diabetes in the NOD model (Weber, C., et al., In: Hardy M. ed. Xenograft/25. Amsterdam: Elsevier, 1989; and Boitard B., et al., J Exp Med 1989 169:1669).

While there may be a systemic reaction to microencapsulated islet xenografts, the intensity of the observed cellular reaction immediately surrounding the microcapsule is remarkable. It is well established that a number of cytokines (IFN-gamma and IL-2) and monokines (IL-1 and TNF) alter or damage islet cells. Pujol-Borrel et al. (Pujol-Borrell R., et al., In: Molnar G. and Jaworski M., eds. Proceedings of the Symposium Immunol. Diabetes, June, 1986. Amsterdam: Elsevier 1987:89), Wright et al. (Wright J., et al., Diabetes 1986 35:1174) and Varey et al. (Varey A., et al., Diabetes 1988 37:209) have shown that IFN-gamma mediates 1a (class II MHC) antigen expression on beta cells; and Koivisto et al. (Koivisto V., et al., Diabetes 1989 38:641) have shown that inferon impairs glucose tolerance and insulin sensitivity in man. Interleukin-1, which may be induced by IFN-gamma, has been shown to inhibit insulin secretion from isolated rat islets (Zawalich W. and Diaz V., Diabetes 1986 35:1119) and to be directly toxic to murine beta cells (Mandrup-Poulsen T., et al., Diabetologia 1986 29:63).

Interleukin-2 is known to activate lymphoid (NK) cells cytotoxic for BB/rat islet cells (Rikel C., et al., Diabetes 1987; 36: 1217). Furthermore, it has been shown recently that administration of a MoAb specific for the IL-2 receptor on activated lymphocytes suppresses insulitis in NOD mice (Kelley V., et al., J. Immunol 1988 140:59). It is likely that, once recruited to the surroundings of the microcapsule, lymphokine-secreting cells injured donor islets via these soluble factors.

Histologic studies of microcapsules in applicants' preliminary experiments have shown that occasional microcapsules appear to have broken prior to applicants' biopsy, since host lymphocytes are clearly within the capsule. Examination of preparations of microencapsulated donor islets prior to grafting occasionally shows a rare donor islet that is not encapsulated. It is nearly impossible to eliminate such technical errors without discarding large portions of a preparation, and that is impractical.

Applicants assume that they have sensitized the NOD recipient with most encapsulated xenografts. However, the degree to which this presumed sensitization influences graft survival is not known.

EXPERIMENT 3

Prolonged Functional Survival of Rat-to-nod Mouse Islet Xenografts by Ultraviolet—B (UV-B) Irradiation Plus Microencapsulation (M) of Donor Islets (See FIGS. 22 to 29)

The goal of this experiment was to clarify the mechanism of destruction of microencapsulated islet xenografts by NOD mice. Several recent studies have found long-term survival of xenogeneic islets in chemically-diabetic mice, with use of (M). However, applicants found that NOD mice destroyed rat islet xenografts in spite of (M), in 10±2 days (N=7), with graft biopsies revealing an intense cellular reaction, not seen when empty (M) were implanted. Companion experiments with recipient helper T-cell depletion showed long-term xenograft function and absence of cellular reaction. Applicants postulated that MHC antigen(s) released from the encapsulated islet cells were provoking the cellular reaction. Since recipient diabetic treatment anti-helper T-cell therapy is undesirable, applicants chose to combine donor islet (M) with (UV-B), since previous studies have suggested reduced donor islet immunogenicity after (UV-B). Donor rat islets (1500/graft) were treated with 600 J (UV-B), 48 hours prior to (M) and intraperitoneal xenografting into stable NOD mice. Control NOD mice received 800-1100 donor rat islets intrasplenically, after 48 hours of tissue culture, with (N=3) or without (N=5) pretreatment with (UV-B). Empty (M) were implanted in 4 pre-diabetic NODs, and followed for 6 months. Random tail vein blood glucose (BG) was below 200 mg/dl within 24 hours in all recipients of islets. Graft rejection was defined as the first day BG exceeded 250 mg/dl. The technique of (M) included 1.7% Na alginate, and two layers of 18,000 M.W. poly-l-lysine. Unmodified rat islets xenografted intrasplenically, without (M), functioned for 3, 4, 4, 5, 5 days. (UV-B)—treated rat islets, without (M), functioned for 5, 5, 5 days, respectively. Biopsies of splenic grafts, done within 2 days after rejection, revealed no viable donor islets. Rat islets xenografted intraperitoneally, with (UV-B) and (M) functioned 24, 47, 47, 98 and 136 days. Biopsies of long-term surviving grafts, on day #90, revealed no cellular reaction, and viable donor islets within intact (M). Biopsies of grafts failing on 24 and 47 days showed a mild cellular reaction, composed primarily of lymphocytes, and some clearly viable donor rat islets within (M). At eventual graft failure, biopsies of two long-term surviving grafts of (UV-B)—treated rat islet xenografts, with (M), revealed very limited, focal cellular reaction, occasional damaged (M) and occasional viable islets. Empty (M) biopsied after 185 days intraperitoneally in pre-diabetic NODs were uniformly intact, and without any cellular reaction (N=4). Applicants conclude that the techniques of (UV-B) and (M) are synergistic in prevention of destruction of rat islet xenografts in NOD mice. Applicants hypothesize that this synergy is based on primary protection of donor islets from rejection by (M), and the known alteration of islet immunogenicity by (UV-B), which may protect (M) islets from autoimmune destruction by the spontaneously diabetic NOD mouse.

What is claimed is:

1. A double-walled bead produced as a result of a method of encapsulating viable tissue or cells within a double-walled bead comprising:

(a) treating the tissue or cells, prior to encapsulation, with ultraviolet-B irradiation so as to immunosuppress them;

(b) suspending the tissue or cells in an aqueous medium which is physiologically compatible with the tissue or cells and which contains a water soluble substance which (i) is physiologically compatible with the tissue or cells; and (ii) can be gelled to form a bead;

(c) forming the suspension into droplets of a size sufficient to encapsulate the tissue or cells;

(d) treating the droplets so as to form discrete, shape-retaining temporary capsules;

(e) forming a permanent semipermeable membrane around the temporary capsules so as to obtain a single-walled bead encapsulating the tissue or cells; and (f) contacting the resulting single-walled bead with the water soluble substance under conditions such that a second membrane is formed so as to thereby obtain a double-walled bead encapsulating the tissue or cells.

2. The double-walled bead of claim 1, wherein the tissue or cells comprise pancreatic islets.

3. The double-walled bead of claim 2 wherein the pancreatic islets are from an animal distantly related or unrelated to a human being.

4. The double-walled bead of claim 1, wherein in step (b) the water soluble substance comprises a gum.

5. The double-walled bead of claim 4, wherein the gum comprises an alkali metal alginate.

6. The double-walled bead of claim 1, wherein in step (d) the treatment of the droplets comprises subjecting the droplets to a solution of multivalent cations.

7. The double-walled bead of claim 6 wherein the multivalent cations solution comprises a calcium solution.

8. The double-walled bead of claim 4, wherein in step (e) the membrane is formed by subjecting the temporary capsules to polymer containing substituents reactive with the acid groups of the gum.

9. The double-walled bead of claim 8, wherein the polymer is a polyamino acid.

10. The double-walled bead of claim 9, wherein the polyamino acid is polylysine.

11. The double-walled bead of claim 10, wherein the polyamino acid is poly-l-lysine with a molecular weight between about 18 Kd and about 57 Kd.

12. The double-walled bead of claim 1, wherein the treatment of the tissue or cells in step (a) may alternatively comprise contacting the tissue or cells with cyclosporine.

* * * * *